(12) United States Patent
Talavera-Peraza

(10) Patent No.: US 9,907,635 B2
(45) Date of Patent: Mar. 6, 2018

(54) GAUZE PAD HOLDER FOR POST-SURGICAL INTRAORAL USE

(71) Applicant: Cesar Talavera-Peraza, Hatillo, PR (US)

(72) Inventor: Cesar Talavera-Peraza, Hatillo, PR (US)

( * ) Notice: Subject to any disclaimer, the term of this patent is extended or adjusted under 35 U.S.C. 154(b) by 8 days.

(21) Appl. No.: 15/180,021

(22) Filed: Jun. 11, 2016

(65) Prior Publication Data

US 2017/0354486 A1 Dec. 14, 2017

(51) Int. Cl.
*A61C 19/00* (2006.01)
*A61C 19/02* (2006.01)

(52) U.S. Cl.
CPC .......... *A61C 19/001* (2013.01); *A61C 19/02* (2013.01)

(58) Field of Classification Search
CPC ............................ A61C 19/001; A61C 19/02
See application file for complete search history.

(56) References Cited

U.S. PATENT DOCUMENTS

| | | | | |
|---|---|---|---|---|
| 1,010,147 A * | 11/1911 | Ivory | ............ | A61C 19/001 433/138 |
| 2,623,284 A * | 12/1952 | Ackley | ............ | A61C 19/001 433/138 |
| 2,791,030 A * | 5/1957 | Tofflemire | ............ | A61C 17/043 433/138 |
| 2,914,852 A * | 12/1959 | Fridge, Sr. | ............ | A61C 19/001 433/138 |
| 3,101,543 A * | 8/1963 | Baughan | ............ | A61C 17/043 433/94 |
| 3,324,855 A * | 6/1967 | Heimlich | ............ | A61B 17/02 401/133 |
| 3,353,227 A * | 11/1967 | Kabel | ............ | B65B 13/345 24/16 PB |
| 3,705,585 A * | 12/1972 | Saffro | ............ | A61F 13/2008 433/136 |
| 3,819,139 A * | 6/1974 | Jemison | ............ | F16L 3/14 24/16 PB |
| 3,936,129 A * | 2/1976 | Guy | ............ | H01R 13/516 174/138 F |
| 3,971,105 A * | 7/1976 | Caveney | ............ | H02G 3/32 24/16 PB |
| 4,221,352 A * | 9/1980 | Caveney | ............ | H02G 3/32 248/74.3 |
| 4,325,526 A * | 4/1982 | Kitagawa | ............ | F16L 3/23 24/336 |
| 5,817,121 A * | 10/1998 | Christoudias | ............ | A61B 17/00234 604/1 |
| 6,443,959 B1* | 9/2002 | Beland | ............ | A61B 17/221 606/127 |

(Continued)

*Primary Examiner* — Cris L Rodriguez
*Assistant Examiner* — Hao D Mai
(74) *Attorney, Agent, or Firm* — Hector M. Reyes Rivera

(57) ABSTRACT

A holder for safely securing a gauze pad for use in a post-surgical area in the intraoral cavity of a patient in order to allow a blood clot to form in safe, hygienic and sanitary conditions. The holder provides a holding cavity wherein the gauze pad is secured and held. It also requires a handle section that allows the external control of the gauze pad by the patient. Embodiments having holding sections with different ergonomic shapes according to the particular position of the intraoral surgical area requiring placement of the gauze pad are described.

40 Claims, 27 Drawing Sheets

(56) References Cited

U.S. PATENT DOCUMENTS

| | | | | |
|---|---|---|---|---|
| 6,464,181 | B2* | 10/2002 | Sakakura | F16L 3/23 24/16 PB |
| 7,328,705 | B2* | 2/2008 | Abramson | A61F 5/566 128/206.11 |
| 8,157,832 | B2* | 4/2012 | Refai | A61B 17/28 606/190 |
| 9,387,060 | B2* | 7/2016 | Talavera-Peraza | A61C 19/001 |
| 9,512,940 | B2* | 12/2016 | Blakeley | H02G 3/32 |
| 9,538,995 | B2* | 1/2017 | Crenshaw | A61B 17/00 |
| 9,592,069 | B2* | 3/2017 | Moody | A61B 17/320016 |
| 2004/0243073 | A1* | 12/2004 | Lockwood | A61M 1/0084 604/313 |
| 2006/0264987 | A1* | 11/2006 | Sgro | A61B 17/12013 606/157 |
| 2009/0106945 | A1* | 4/2009 | Ahrenholtz | A45F 5/04 24/7 |
| 2016/0038200 | A1* | 2/2016 | Knoepfle | A61B 17/82 606/324 |

* cited by examiner

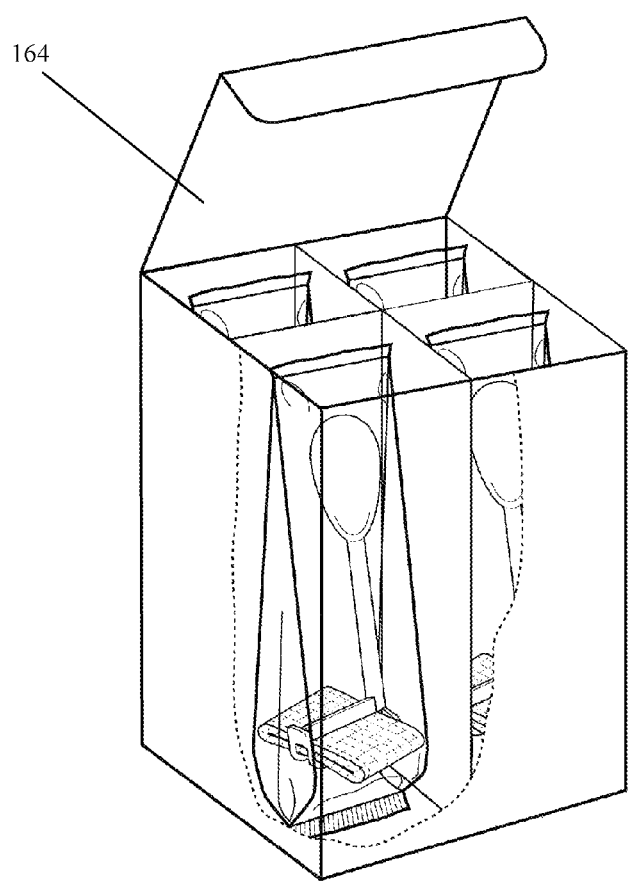 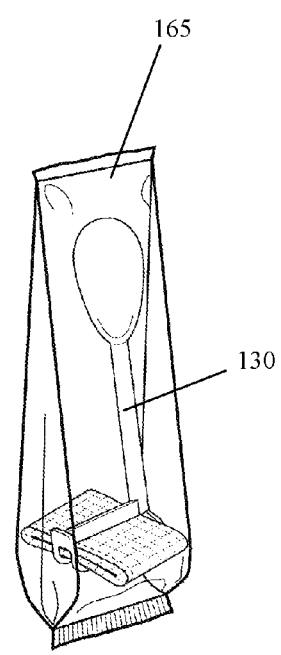
FIG. 53                   FIG. 54

GAUZE PAD HOLDER FOR POST-SURGICAL INTRAORAL USE

TECHNICAL FIELD OF THE INVENTION

This invention relates to gauze pad holders. More particular, the invention is directed to gauze pad holders useful in securing and holding a gauze pad at a particular area of the mouth after a surgical procedure has been performed in the intraoral cavity.

BACKGROUND OF THE INVENTION

Surgical procedures inside the mouth, such as tooth extractions, generally cause more bleeding than a skin wound due to the difficulty associated with the process of drying out the gums and thus delaying the blood clot formation, which is an essential initial step of the post extraction healing process. Said blood clot is formed inside the hole or socket in the bone where the tooth has been removed, essentially at the site of a tooth extraction. This blood clot serves as a protective layer over the underlying bone and nerve endings in the empty tooth socket. The clot also provides the foundation for the growth of new bone and for the development of soft tissue over the clot.

Unfortunately, due to different factors, the blood clot at the site of the tooth extraction is not always properly formed and/or developed. For instance, it may be dislodged or dissolved before the wound has healed. As a consequence, there is an exposure of the underlying bone and nerves to air, food, fluid, bacteria or any other potential organisms that results in intense pain, not only in the socket but also along the nerves radiating to the side of your face. Such condition may produce excess bleeding and more importantly is responsible for the medical condition known as alveolar osteitis or commonly called "dry socket". Therefore, promoting a safe healing process requires a healthy and hygienic environment for the proper formation of the blood clot.

In order to control the bleeding after the intraoral surgical procedure is performed and more particularly, to promote a properly blood clot formation in the right position of the socket; a common practice is to place a gauze pad over the dental extraction site and bite on it for about 30 minutes, so that pressure is applied to the surgical area in order to maintain a dry field and allow a blood clot to form.

Said procedure has a series of disadvantages. For instance, said gauze pad is usually inserted in the postsurgical intraoral area by healthcare personnel, personal assistants or by the patient himself, generally by introducing their hands into the mouth. This represents a poor hygienic practice that exposes the surgical area to potential pathogens such as bacteria, increasing the chances of opportunistic infections and other postsurgical complications. Indeed, presently, infections involving antibiotic resistant bacteria are a real challenge to treat, thus new preventive measures with the aim of avoiding exposure of such bacteria are an essential part of the standard of care process.

Another potentially dangerous situation is due to the fact that the gauze pad is not secured by any means inside the oral cavity of a patient who is generally under some kind of sedation, said gauze pad may be displaced from the surgical area to the patient's pharynx, causing an obstruction of the patient's airway; thus representing and asphyxiation or choking hazard.

Furthermore, since the patient has no direct visual contact of the surgical site's exact location, there is a high chance that he or she may not be able to place and maintain the gauze pad in the proper location, thus the effect of applying pressure over the desired and specific intraoral area may not be achieved. In a similar manner, after using said gauze pad, it is uncomfortable and unpleasant to remove it from the mouth, since it is soaked with blood and saliva. Moreover, in order for the gauze pad to be effective in the postsurgical intraoral area, the gauzes should be folded properly in a square shape by folding the gauzes in half twice so that the resulting gauze pad is ideal for the placement over the extraction site. Therefore, there is a need to provide a suitable hygienic and sanitary gauze pad holder that allows the control of a gauze pad over a particular and specific postsurgical intraoral area.

OBJECTS AND SUMMARY OF THE INVENTION

It is an object of the invention to provide a gauze pad holder that allows placing gauze pads properly in a post-surgical intraoral area in safe, hygienic and sanitary conditions. It is another object of the invention to provide a preventive measure with the aim of avoiding exposure of antibiotic resistant bacteria after intraoral surgical procedures.

Yet another object of the invention is to provide a holder for a gauze pad that allows the blood clot to be stable inside the tooth socket, minimizing the risk of it to be dislodged and thus preventing the formation of the development of a dry socket and or excess bleeding.

Another object of the invention is to provide a gauze pad holder that eliminates the need of using direct hand contact in order to properly place said gauze pad in the oral cavity of a patient. Another object of the invention is to provide a gauze pad holder that allows maintaining said gauze pad over the post-surgical intraoral area providing a safe positioning that avoids the gauze pad displacement from said particular area in order to increase the effectiveness of the gauze pad in stopping the gums from bleeding and avoiding potential choking of the patient caused by said gauze pad. Yet another object of the invention is to provide a gauze pad holder that allows external patient control of the pad by the patient, eliminating the need of inserting fingers in the patient's oral cavity to re-accommodate said pad, thus providing a sense of security and comfort to the patient. Another object of the invention is to provide a gauze pad holder that allows maintaining the proper folding and shape of the pad during the process that said pad is used in order to ensure ideal contact of said pad over the surgical site. Yet another object of the invention is to provide a gauze pad holder with an extra locking mechanism of securing the gauze pad in place. Still another object of the invention is to provide a gauze pad holder that is ergonomically designed in order to be comfortably positioned over a post-surgical intraoral area according to the nature and surroundings of said intraoral area. Thus, embodiments having different shapes are presented, preferably to be used in molar, pre-molar or anterior teeth positions. In yet another object of the invention is to provide a gauze pad holder for intraoral use that is easy to be removed or substituted after being used without the need of inserting fingers into the oral cavity. In yet another object of the invention is to provide an already disinfected, sanitary gauze pad which is firmly secured to said holder that is ready to be used in safe, hygienic and sanitary conditions.

BRIEF DESCRIPTION OF THE DRAWINGS

The foregoing and additional features and characteristics of the present invention will become more apparent from the following detailed description considered with reference to the accompanying drawings, wherein:

FIG. 53 illustrates a diagrammatical representation of sanitary and disposable kit having a predetermined amount of units comprising a holder illustrated in FIG. 26, wherein the enclosure of said kit has been cut off in order to shows its details.

FIG. 54 shows a diagrammatical representation of individually wrapped embodiment of the pad holder illustrated in FIG. 26 and enclosed in the sanitary and disposable kit illustrated in FIG. 53.

DETAILED DESCRIPTION OF THE EMBODIMENTS

The following detailed description illustrates the invention and a variety of embodiments by way of example and is not limited to the particular limitations presented herein as principles of the invention. This description is directed to enable one skilled in the art to make and use the invention by describing embodiments, adaptations, variations and alternatives of the invention. Any potential variations of the limitations herein described are within the scope of the invention.

In general terms, the instant invention is directed to a gauze pad holder, useful in holding a gauze pad, which is intended to be pressed or bitten in a post-surgical precise location inside the mouth, just after a surgical dental procedure has been performed. Thus, a section of the holder has been intended to be used intraoral and for instance, after tooth extraction. The instant invention comprises different embodiments able to adapt to the particular intraoral post-surgical location due to the curvature of the oral cavity and different elements may be included to further secure said gauze pad firmly in a particular area of the mouth after surgical procedure.

Figure 1:
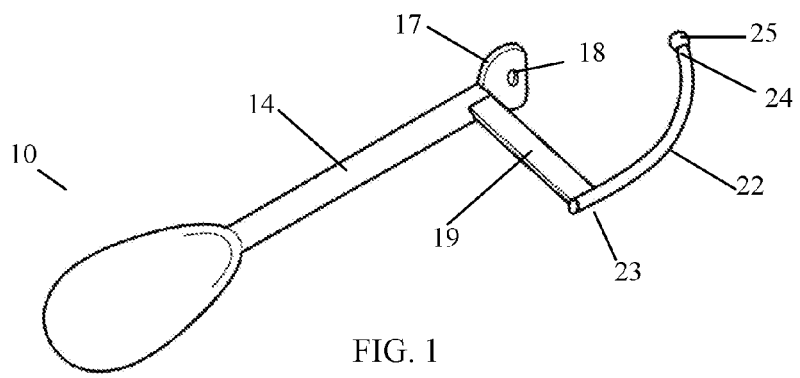
FIG. 1 shows a diagrammatical representation in a perspective view of one embodiment of the gauze pad holder according to the invention in an open position.
Figure 2:
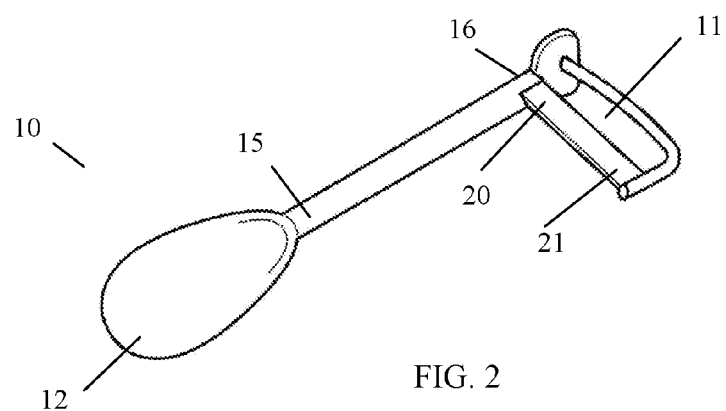
FIG. 2 illustrates a diagrammatical representation in a perspective view of the embodiment of the gauze pad holder according to the invention illustrated in FIG. 1 in closed position, showing the internal cavity or chamber wherein the gauze pad may be held and secured.
Figure 3:
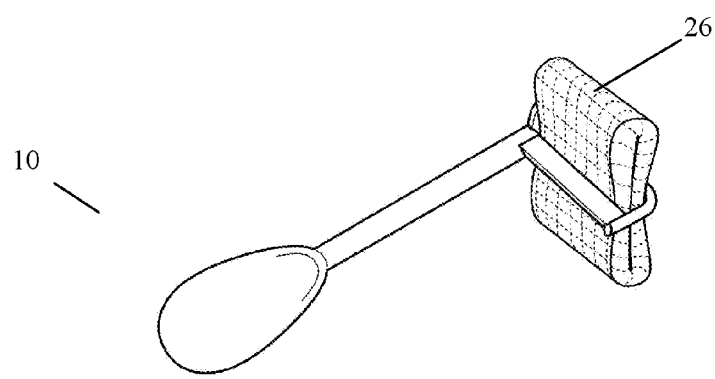
FIG. 3 shows a diagrammatical representation in a perspective view of one embodiment of the gauze pad holder illustrated in FIGS. 1 and 2 having a gauze pad already assembled in its internal cavity.

The first embodiment of the invention 10 is illustrated in FIG. 1 in open position; in FIG. 2 in a closed position, in order to show the internal cavity or chamber, wherein the gauze pad may be held and secured and in FIG. 3, wherein it has already a gauze pad assembled, held and secured in its internal cavity or chamber 11.

Particularly and as illustrated in FIGS. 1 and 2, it comprises a handle section 12, which is illustrated having a preferably flat, oval shape with a concave center surrounded by round edges; although it may have any other suitable shape. Extending from handle section 12, it also comprises connecting section 14, which has an elongated body, having a preferably cylindrical shape; a first end 15, wherein it is connected to handle 12 and a second end 16, which it is connected to first holding section 17.

First holding section 17 comprises a flat main body, having aperture 18 at the center or substantially the center of said main body of first holding section 17. Thus, first holding section 17 is located aligned or substantially aligned to handle 12. Embodiment 10 also comprises supporting section 19 having an elongated body, which is preferably rectangular; a first end 20, which is attached perpendicularly at the right side area of the second end 16 of the connecting section 14 and a second end 21. Embodiment 10 also comprises a second holding section 22, which comprises an elongated flexible body having a first end 23 which is connected to the second end 21 of said connecting section; a second end 24 and a sphere-shaped section 25, which is connected to said second end 24. Second holding section 22 is positioned in a parallel position with reference to the first holding section 17.

As illustrated in FIG. 2, internal cavity or chamber 11, capable of holding a gauze pad 26 is formed by inserting the sphere-shaped section 25 positioned at the second end 24 of said elongated flexible body of the second holding section 22 inside the aperture 18 on the flat main body of the first holding section 17. Said insertion of sphere shaped section 25 on aperture 18 in a male-female fasting mechanism is a non-permanent connection and said interconnection may be substituted by any other suitable nonpermanent connection. Internal cavity or chamber 11 is located in a perpendicular position with reference to the handle 12 and connecting section 14, thus, as illustrated in FIG. 3, gauze pad 26 is also positioned in a perpendicular position with regard to handle 12 and connecting section 14.

Figure 4:
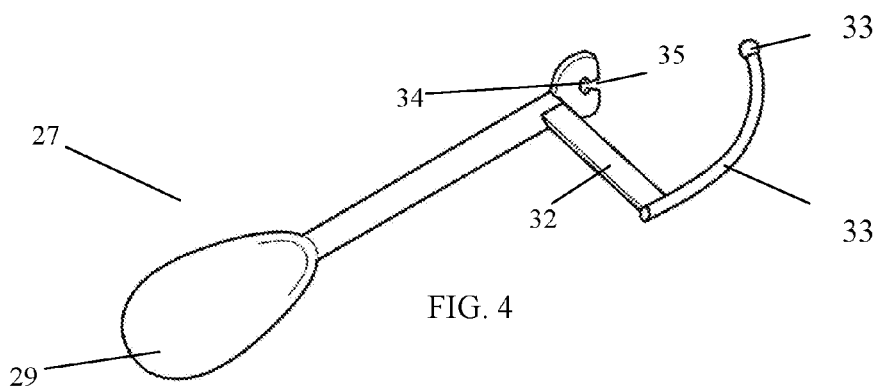
FIG. 4 shows a diagrammatical representation in a perspective view of one embodiment of the gauze pad holder according to the invention in an open position.
Figure 5:
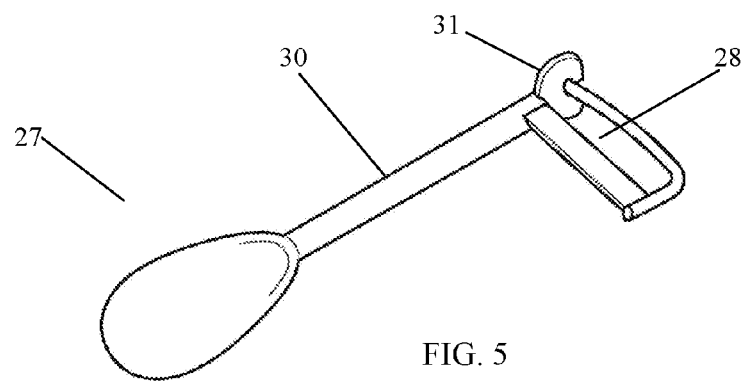
FIG. 5 illustrates a diagrammatical representation in a perspective view of the embodiment of the gauze pad holder according to the invention illustrated in FIG. 4 in closed position, showing the internal cavity or chamber wherein the gauze pad may be held and secured.
Figure 6:
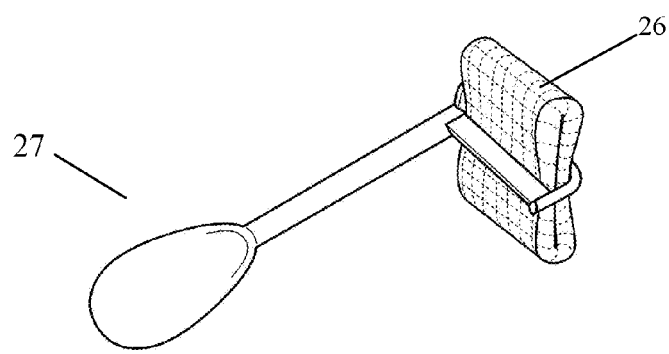
FIG. 6 shows a diagrammatical representation in a perspective view of one embodiment of the gauze pad holder illustrated in FIGS. 4 and 5 having a gauze pad already assembled in its internal cavity.

A second embodiment 27 according to the instant invention is illustrated in FIGS. 4, 5 and 6. In FIG. 4 it is shown in open position while in FIG. 5 is represented in a closed position, illustrating internal cavity or chamber 28. In FIG. 6, said second embodiment is shown having a gauze pad already assembled, held and secured in its internal cavity or chamber 28.

Embodiment 27 shares almost all the elements or sections already discussed above for embodiment 10: it comprises a handle section 29, a connection section 30, a supporting section 32, a first holding section 31 and a second holding section 33. All said sections having the same structural details previously for embodiment 10 with the exception of first holding section 31.

As illustrated in FIGS. 4 and 5, first holding unit 31 comprises a main flat body having a round aperture 34 at the center or substantially the center of said main body. It also comprises a wedge shaped groove 35 which is in direct contact with round aperture 34. Groove 35 provides an enter or a channel for said round aperture 34 to the exterior of the main body of 31, from wherein the external flexible body of second holding section 33 may be inserted in order to provide internal cavity 28 of embodiment 27, as illustrated in FIG. 5.

Figure 7:
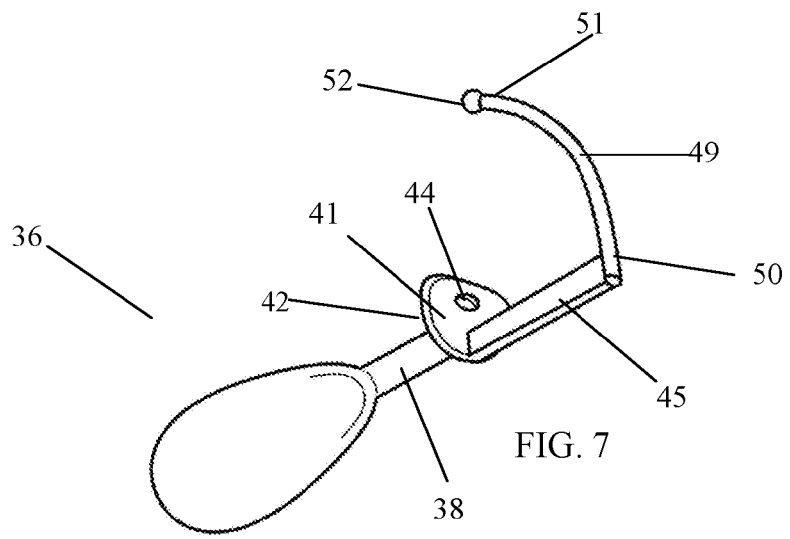
FIG. 7 shows a diagrammatical representation in a perspective view of one embodiment of the gauze pad holder according to the invention in an open position.
Figure 8:
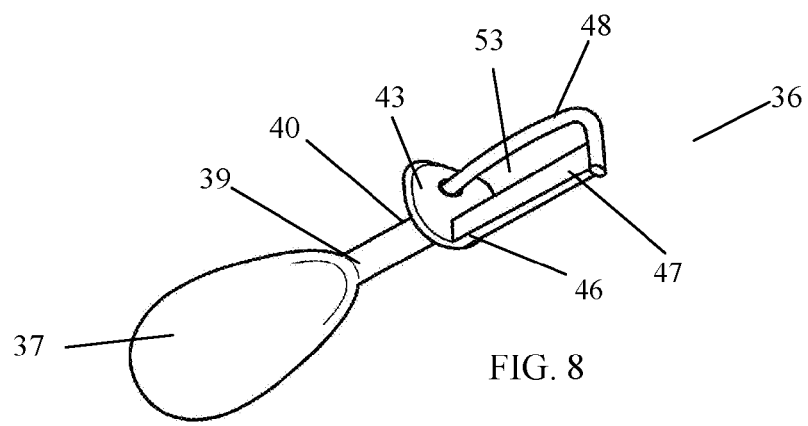
FIG. 8 illustrates a diagrammatical representation in a perspective view of the embodiment of the gauze pad holder according to the invention illustrated in FIG. 7 in closed position, showing the internal cavity or chamber wherein the gauze pad may be held and secured.

FIGS. 7 and 8 illustrates also embodiment 36 in open and closed configuration respectively. On FIG. 9, embodiment 36 is shown having a gauze pad already assembled held and secured. Embodiment 36 comprises a handle section 37, which is illustrated having a preferably flat, oval shape with a concave center surrounded by round edges; although it may have any other suitable shape. Extending from handle section 37, it also comprises connecting section 38, which has an elongated body of preferably cylindrical shape, a first end 39, wherein it is connected to handle section 37 and a second end 40. Embodiment 36 comprises a first holding section 41, which comprises a flat main body having a front surface 42 and a back surface 43 in reference to handle section 37 and aperture or opening 44. Second end 40 of connecting section 38 is connected to the front surface 42 of main body of first holding section 41. Embodiment 36 also comprises supporting section 45 having its first end 46 connected to the back surface 43 of said first holding section and its second end 47. Embodiment 36 also comprises a second holding section 48, having a flexible elongated body 49, a first end 50 and a second end 51. Said first end 50 of the second holding section 48 is connected to the second end 47 of supporting section 45. Connected to said second end 51, is a spherical shaped section 52.

Figure 9:
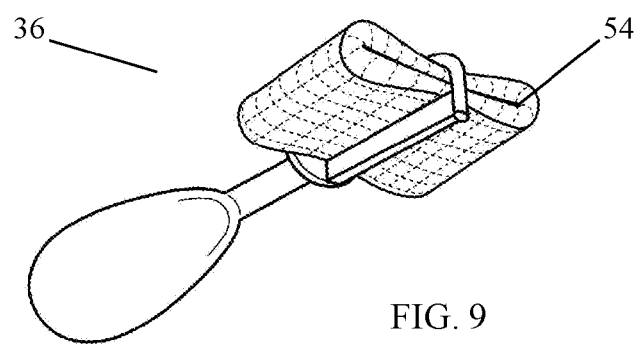
FIG. 9 shows a diagrammatical representation in a perspective view of one embodiment of the gauze pad holder illustrated in FIGS. 7 and 8 having a gauze pad already assembled in its internal cavity.

As illustrated in FIG. 8, once spherical section 50 is inserted on aperture 44, an internal cavity or chamber 53 wherein a gauze pad 54 may be held is created. As illustrated in FIG. 9, in embodiment 36, the handle section 37, the connecting section 38 and internal cavity 53 are in an aligned position in reference to one another.

Figure 10:
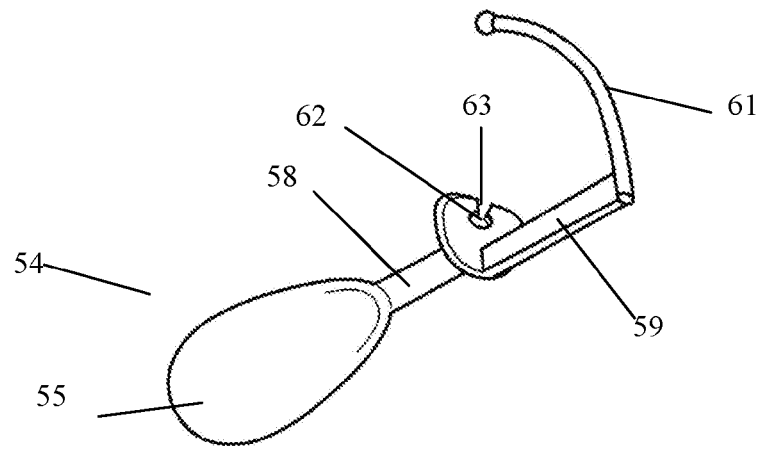
FIG. 10 shows a diagrammatical representation in a perspective view of one embodiment of the gauze pad holder according to the invention in an open position.
Figure 11:
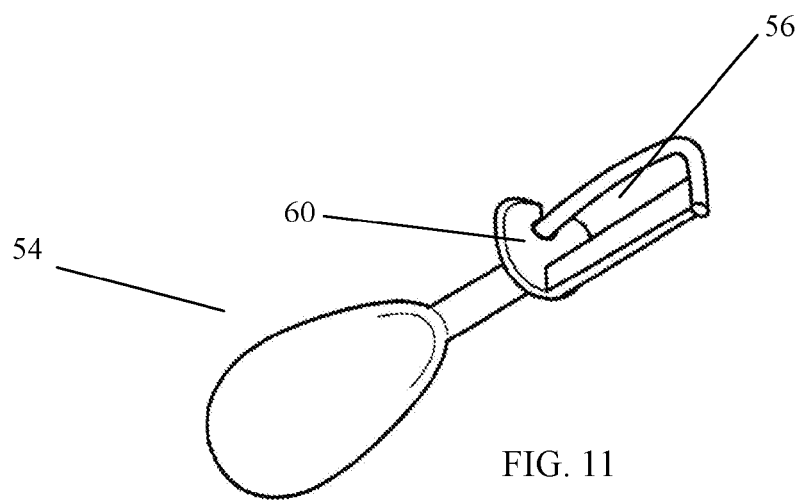
FIG. 11 illustrates a diagrammatical representation in a perspective view of the embodiment of the gauze pad holder according to the invention illustrated in FIG. 10 in closed position, showing the internal cavity or chamber wherein the gauze pad may be held and secured.
Figure 12:
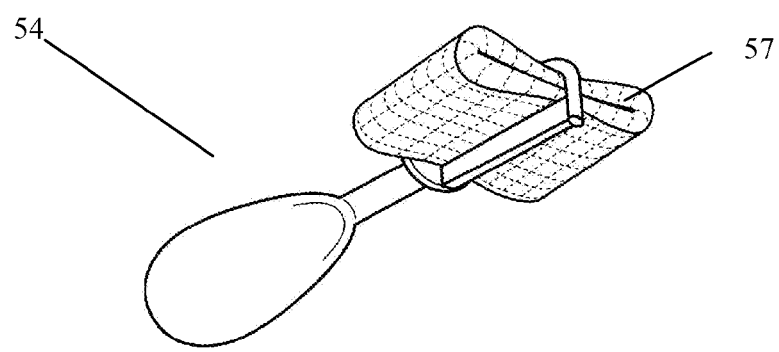
FIG. 12 shows a diagrammatical representation in a perspective view of one embodiment of the gauze pad holder illustrated in FIGS. 10 and 11 having a gauze pad already assembled in its internal cavity.

Embodiment 54 according to the instant invention is illustrated in FIGS. 10, 11 and 12. In FIG. 10 it is shown in open position while in FIG. 11 is represented in a closed position, illustrating internal cavity or chamber 56. In FIG. 12, said second embodiment is shown having a gauze pad already assembled, held and secured in its internal cavity or chamber 56.

Embodiment 54 shares almost all the elements or sections already discussed above for embodiment 36: it comprises a handle section 55, a connecting section 58, a supporting section 59, a first holding section 60 and a second holding section 61. All said sections having the same structural details previously for embodiment 36 with the exception of first holding section 60.

As illustrated in FIGS. 10 and 11, first holding unit 60 comprises a main flat body having a round aperture 62 at the center or substantially the center of said main body. It also comprises a wedge shaped groove 63, which is in direct contact with round aperture 62. Groove 63 provides an enter or a channel for said round aperture 62 to the exterior of the main body of 60, from wherein the external flexible body of second holding section 61 may be inserted in order to provide internal cavity 56 of embodiment 54, as illustrated in FIG. 11.

Figure 13:
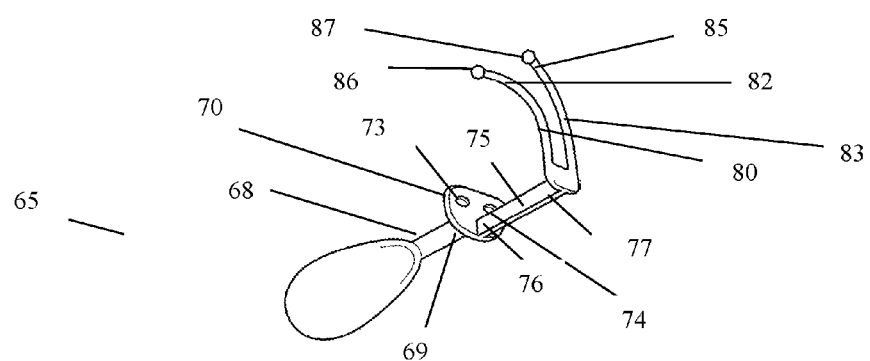
FIG. 13 shows a diagrammatical representation in a perspective view of one embodiment of the gauze pad holder according to the invention in an open position.
Figure 14:
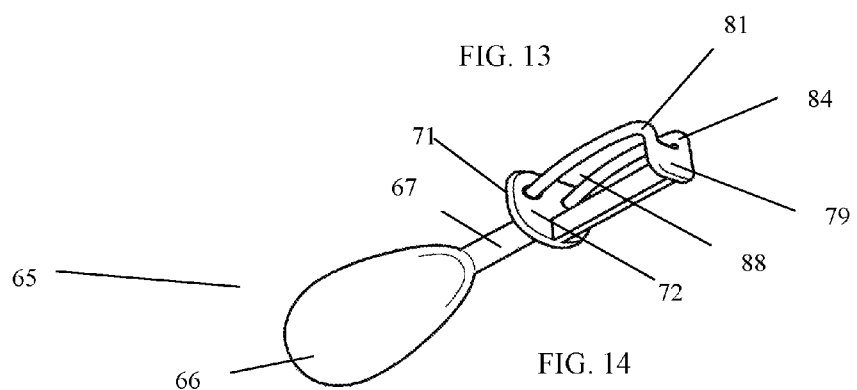
FIG. 14 illustrates a diagrammatical representation in a perspective view of the embodiment of the gauze pad holder according to the invention illustrated in FIG. 13 in closed position, showing the internal cavity or chamber wherein the gauze pad may be held and secured.
Figure 15:
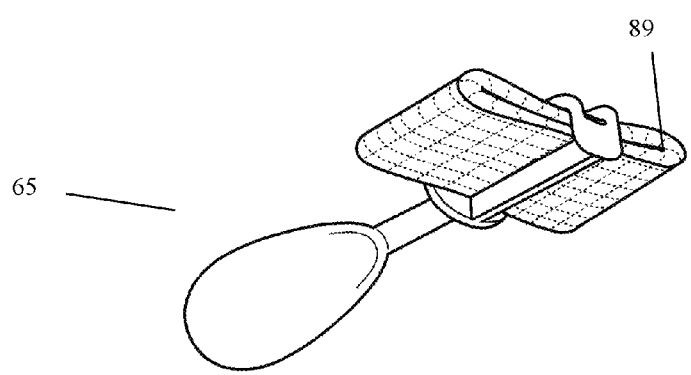
FIG. 15 shows a diagrammatical representation in a perspective view of one embodiment of the gauze pad holder illustrated in FIGS. 13 and 14 having a gauze pad already assembled in its internal cavity.

FIGS. 13 and 14 illustrates also embodiment 65 in open and closed configuration respectively. On FIG. 15, embodiment 65 is shown having a gauze pad 89 already assembled held and secured. Embodiment 65 comprises handle section 66, which is illustrated having a preferably flat, oval shape with a concave center surrounded by round edges; although it may have any other suitable shape. Extending from handle section 66, it also comprises connecting section 67, which has an elongated body of preferably cylindrical shape, a first end 68, which is connected to handle section 66 and a second end 69. Embodiment 65 comprises a first holding section 70, which comprises a flat main body having: a front surface 71 and a back surface 72 in reference to handle section 66; a first aperture or opening 73 and a second aperture 74. Second end 69 of connecting section 67 is connected to the front surface 71 of main body of first holding section 70.

Embodiment 65 also comprises supporting section 75 having its first end 76 connected to the back surface 72 of said first holding section 70 and its second end 77. As illustrated in FIGS. 13 and 14, embodiment 65 also comprises a second holding section 78 having, a base 79 connected to second end 77 of supporting section 75; from base 79 are extended a first flexible elongated body 80 having a first end 81 joined to base 79 and a second end 82 and a second flexible elongated body 83, having a first end 84 joined to base 79 and a second end 85. On the other hand, said second end 82 and second end 85 of the first flexible elongated body 80 and of the second flexible elongated body 83 respectively, are connected to spherical shape sections 86 and 87. Once the spherical shape 86 and 87 are inserted in the first aperture or opening 73 and a second aperture 74 respectively, the internal cavity or chamber 88 is created by joining the first holding section 70 with the second holding section 78. Internal cavity 88 is aligned to handle 66 and to connecting section 67.

Figure 16:
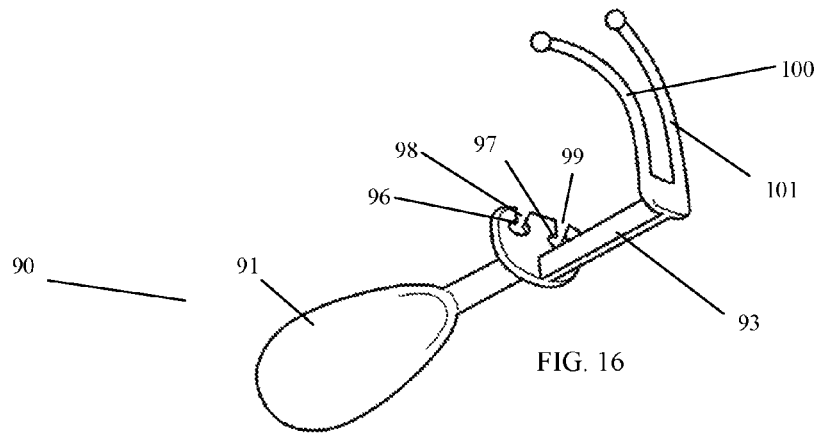
FIG. 16 shows a diagrammatical representation in a perspective view of one embodiment of the gauze pad holder according to the invention in an open position.
Figure 17:
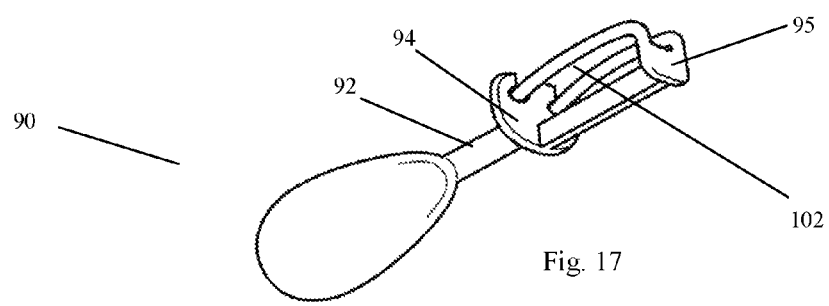
FIG. 17 illustrates a diagrammatical representation in a perspective view of the embodiment of the gauze pad holder according to the invention illustrated in FIG. 16 in closed position, showing the internal cavity or chamber wherein the gauze pad may be held and secured.

As illustrated in FIGS. 16 and 17, embodiment 90 is highly similar to embodiment 65: it shares almost all the elements or sections already discussed above for embodiment 65: it comprises a handle section 91, a connecting section 92, a supporting section 93, a first holding section 94 and a second holding section 95. All said sections having the same structural details previously for embodiment 65, with the exception of first holding section 94.

Figure 18:
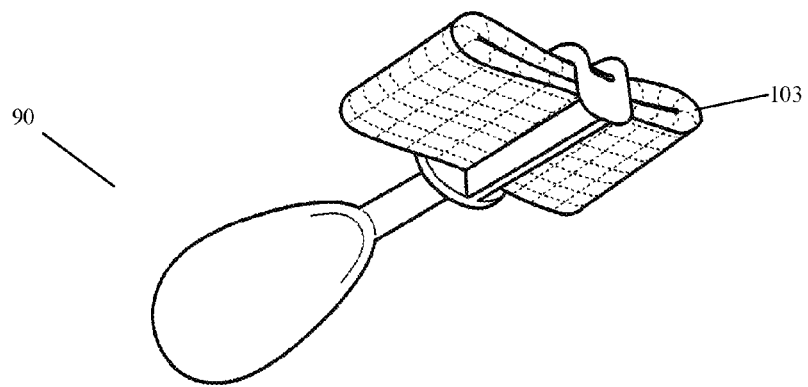
FIG. 18 shows a diagrammatical representation in a perspective view of one embodiment of the gauze pad holder illustrated in FIGS. 16 and 17 having a gauze pad already assembled in its internal cavity.

As illustrated in FIGS. 16 and 17, first holding unit 94 comprises a main flat body having a first round aperture 96 and a second aperture 97 at said main body. It also comprises a first wedge shaped groove 98, which is in direct and open contact with round aperture 96 and a second wedge shaped groove 99, which is direct open contact with aperture 97. Grooves 98 and 99 provides an enter or a channel for said round apertures 96 and 97 respectively, to the exterior of the main body of first holding section 94, from wherein the external flexible bodies 100 and 101 of second holding section 95 may be inserted in order to provide internal cavity 102 of embodiment 90, as illustrated in FIG. 18.

Figure 19:
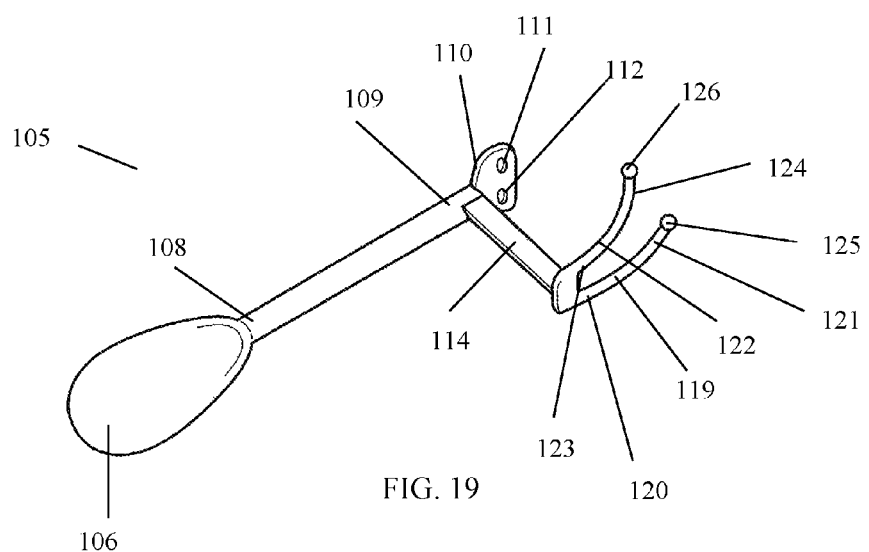
FIG. 19 shows a diagrammatical representation in a perspective view of one embodiment of the gauze pad holder according to the invention in an open position.
Figure 20:
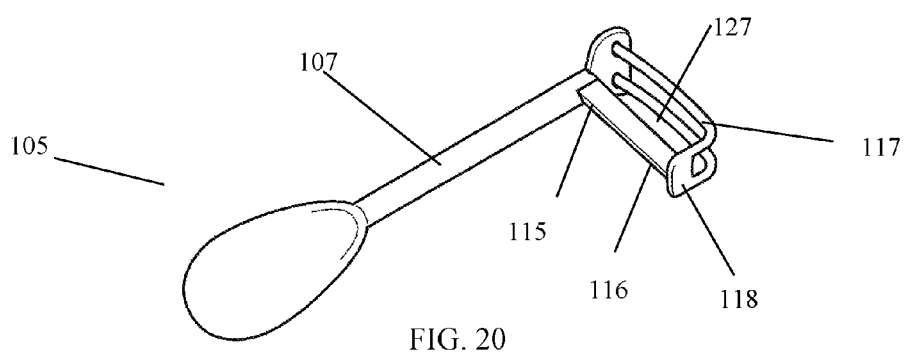
FIG. 20 illustrates a diagrammatical representation in a perspective view of the embodiment of the gauze pad holder according to the invention illustrated in FIG. 19 in closed position, showing the internal cavity or chamber wherein the gauze pad may be held and secured.

Embodiment 105 is illustrated in open and closed configurations in FIGS. 19 and 20 respectively. On FIG. 21 and FIG. 22, embodiment 105 is shown having a gauze pad already assembled held and secured in different folding positions.

Embodiment 105 comprises handle section 106, which is illustrated having a preferably flat, oval shape with a concave center surrounded by round edges; although it may have any other suitable shape. Extending from handle section 106, it also comprises connecting section 107, which has an elongated body of preferably cylindrical shape and having a first end 108, which is connected to handle section 106 and a second end 109. Embodiment 105 comprises a first holding section 110, which comprises a flat main body having a first aperture or opening 111 and a second aperture 112. Second end 109 of connecting section 107 is connected to the main body of first holding section 110.

Embodiment 105 also comprises supporting section 114 having a first end 115 and second end 116. First end 115 of supporting section 114 is connected to the right side of second end section 109 of connecting section 107. Embodiment 105 also comprises second holding section 117 having a base 118 connected to the second end 116 of supporting section 114; a first elongated flexible body 119 having a first end 120 and a second end 121 and a second elongated flexible body 122 having a first end 123 and a second end 124.

First end 120 of first elongated flexible body 119 is connected to the base 118 and first end 123 of second elongated flexible body 122 is also connected to the base 118, being both elongated flexible bodies located in a parallel position in reference to one another. Second end 121 and second end 124 of the first and second flexible bodies 119 and 122, respectively are attached to spherical sections 125 and 126. Once the spherical shape sections 119 and 120 are inserted in the first aperture or opening 111 and a second aperture 112, respectively, the internal cavity or chamber 127 is created by joining the first holding section 110 with the second holding section 117. Internal cavity 127 is perpendicularly positioned in reference to handle 106 and to connecting section 107.

Figure 21:
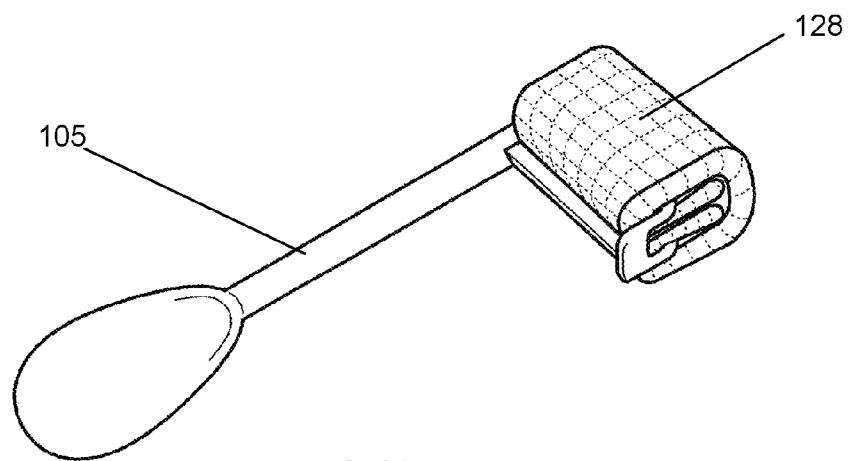
FIG. 21 shows a diagrammatical representation in a perspective view of one embodiment of the gauze pad holder illustrated in FIGS. 19 and 20 having a gauze pad already assembled in its internal cavity.
Figure 22:
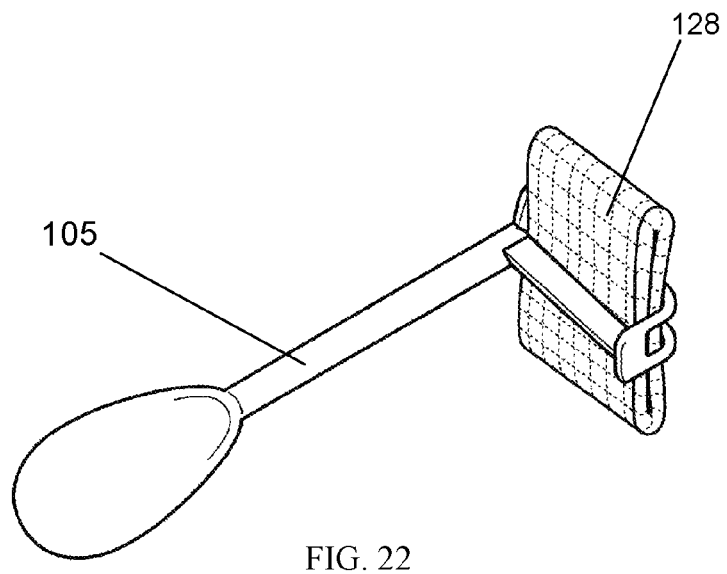
FIG. 22 shows a diagrammatical representation in a perspective view of one embodiment of the gauze pad holder illustrated in FIGS. 19 and 20 having a gauze pad already assembled in an alternative manner in its internal cavity.

As illustrated in FIG. 21, internal cavity or chamber 127 is capable of holding a gauze pad 128 in a folded position surrounding the flexible elongated bodies 119 and 122. Gauze pad 128 may also be assembled in a parallel position to the cavity 127 as illustrated in FIG. 22. In any alternative, gauze pad 128 is held and secured to the holder 105 once the spherical shaped sections 125 and 126 are inserted through the apertures 111 and 112, thus providing a stable positioning of the gauze 128 to the holder 105.

Figure 23:
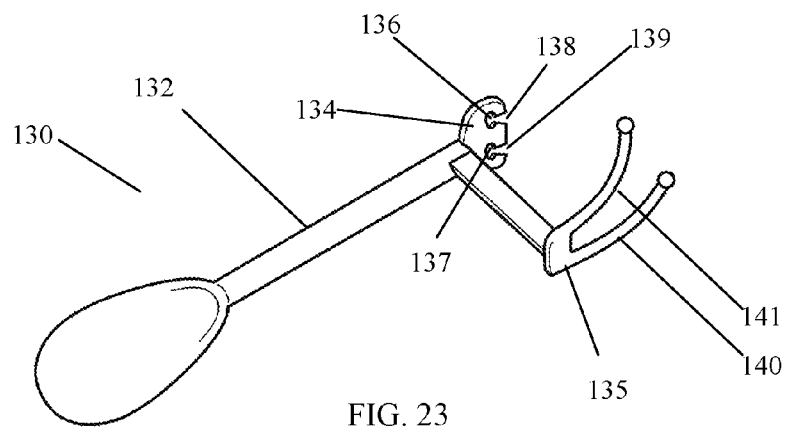
FIG. 23 shows a diagrammatical representation in a perspective view of one embodiment of the gauze pad holder according to the invention in an open position.
Figure 24:
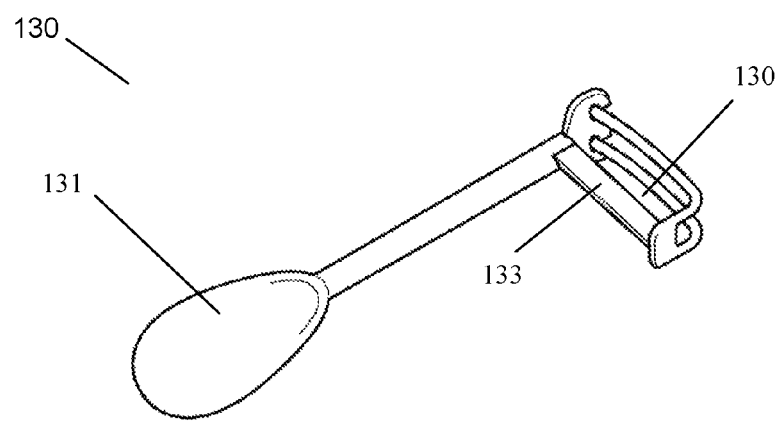
FIG. 24 illustrates a diagrammatical representation in a perspective view of the embodiment of the gauze pad holder according to the invention illustrated in FIG. 23 in closed position, showing the internal cavity or chamber wherein the gauze pad may be held and secured.

FIGS. 23 and 24 illustrates embodiment 130, which is highly similar to embodiment 105: it shares almost all the elements or sections already discussed above for embodiment 105: it comprises a handle section 131, a connecting section 132, a supporting section 133, a first holding section 134 and a second holding section 135. All said sections having the same structural details previously for embodiment 105, with the exception of first holding section 134. As illustrated in FIGS. 23 and 24, first holding unit 134 comprises a main flat body having a first round aperture 136 and a second aperture 137 at said main body. It also comprises a first wedge shaped groove 138, which is in direct open contact with round aperture 136 and a second wedge shaped groove 139, which is in direct and open contact with second aperture 137. Grooves 138 and 139 provides an enter or a channel for said round apertures 136 and 137 respectively, to the exterior of the main body of first holding section 134, from wherein the external flexible bodies 140 and 141 of second holding section 135 may be inserted on order to provide internal cavity 142 of embodiment 130, as illustrated in FIG. 24.

Figure 25:
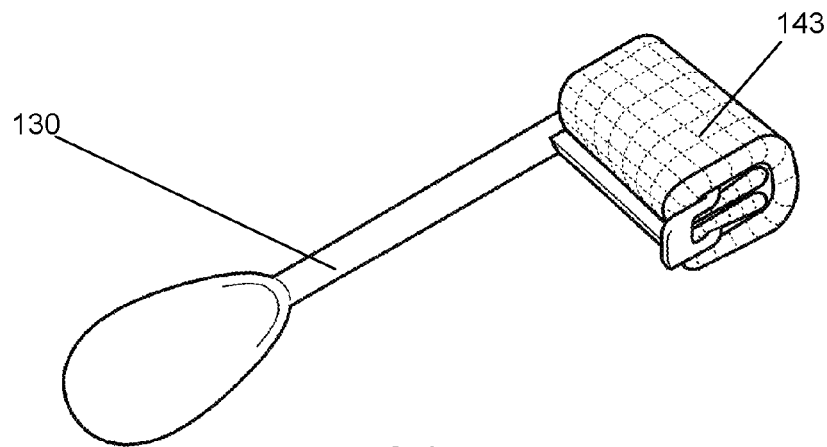
FIG. 25 shows a diagrammatical representation in a perspective view of one embodiment of the gauze pad holder illustrated in FIGS. 23 and 24 having a gauze pad already assembled in its internal cavity.
Figure 26:
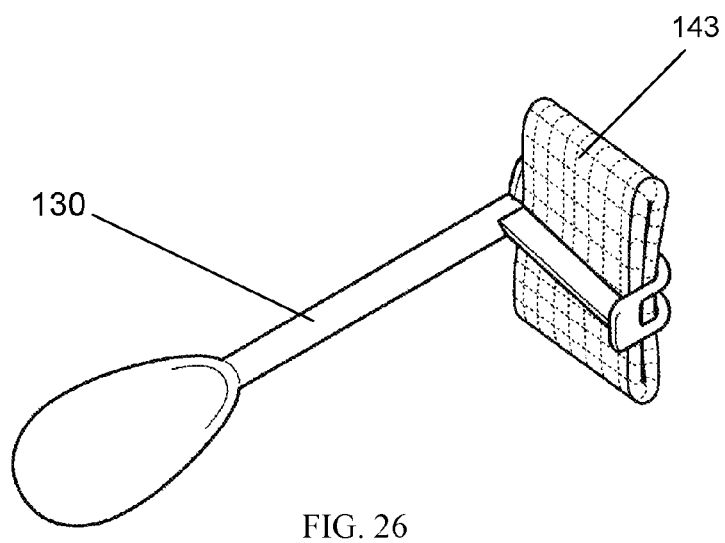
FIG. 26 shows a diagrammatical representation in a perspective view of one embodiment of the gauze pad holder illustrated in FIGS. 23 and 24 having a gauze pad already assembled in an alternative manner in its internal cavity.

As illustrated in FIG. 25, internal cavity or chamber 142 is capable of holding a gauze pad 143 in a folded position surrounding the flexible elongated bodies 140 and 141. Gauze pad 143 may also be assembled in a parallel position to the cavity 142 as illustrated in FIG. 26. In any alternative, gauze pad 143 is held and secured to the holder 130 once the elongated flexible bodies 140 and 141 are inserted through the wedge shaped grooves 138 and 139 respectively and, thus providing a stable positioning of the gauze 143 to the holder 130.

The herein disclosed embodiments 10, 27, 36, 54, 65, 90, 105 and 130 may be made of any suitable strong material, such as plastic or foam, preferably plastic via suitable known in the art molding techniques. It is contemplated that the embodiments may have different sizes since the holder may be used in patients of different ages. It is contemplated that the herein disclosed holder may be for disposable use.

Figure 27:
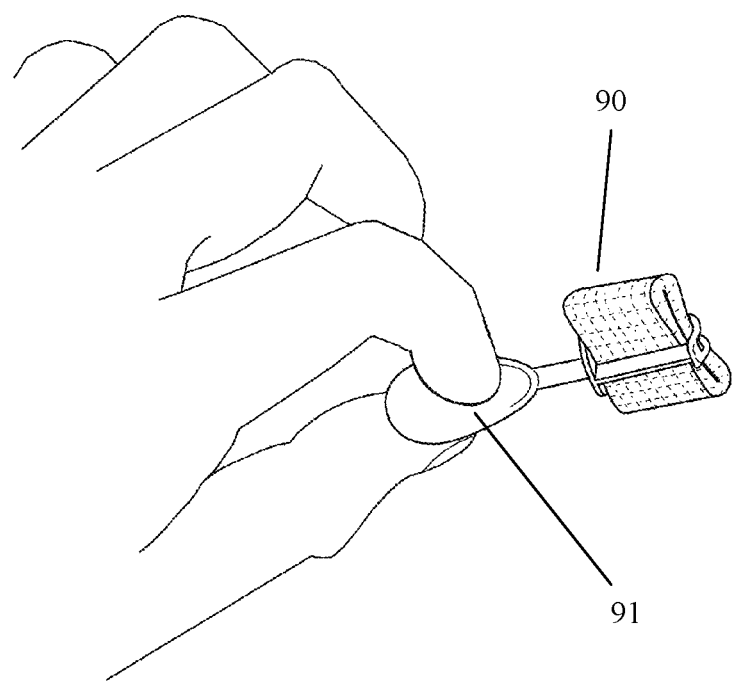
FIGS. 27, 28 and 29 show perspective views illustrating the preferred manner to handle the embodiments of the instant invention.
Figure 28:
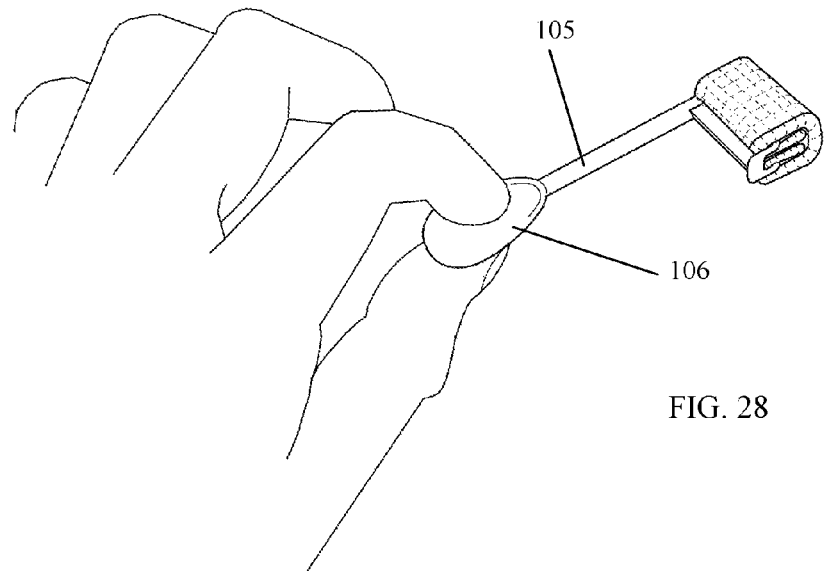
Figure 29:
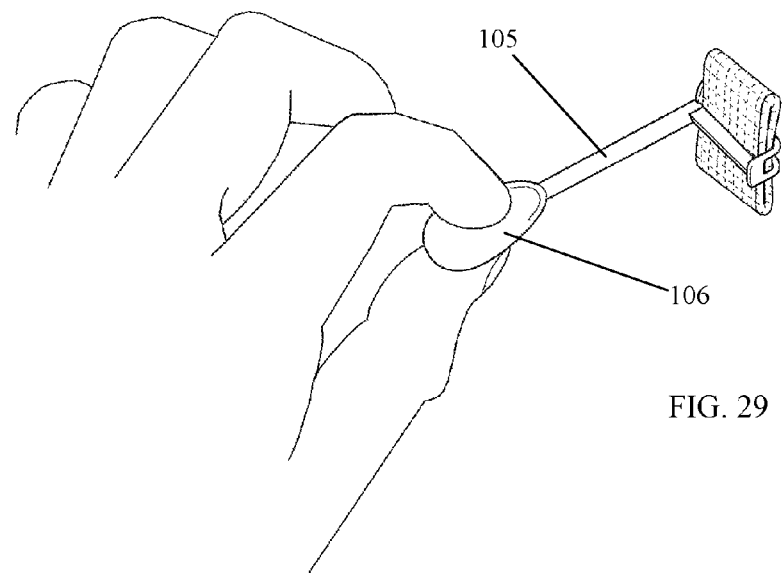

In operational terms, the gauze pad holder is designed so that a cavity is formed after closure of the flexible bodies in each of the embodiments to securely maintain the gauze pad in its ideal folded shape. Such ideal shape is very difficult to attain by the patients themselves who are usually not experts in the oral surgery field. Delegating this task to the patients usually increases the risk of bleeding and other post-operative complications because they do not have the experience to know how to ideally fold the gauze pad depending on the type or location of their surgery. So, the gauze pad holder is a convenient alternative that will be available to patients providing them with a gauze pad that is already ideally folded for them thus bypassing any chance of increasing the likelihood of postoperative complications. As illustrated in FIGS. 27, 28 and 29, and using embodiments 90 and 105 as examples, all embodiments of the gauze holder herein disclosed may be manipulated be means of its handle with no need of touching the gauze and to further provide a hygienic alternative to avoid the need to introduce fingers inside the mouth during the process of placing the gauze pad in the oral cavity. The secured gauze pad in its holder has an ergonomic shape that is necessary to obtain full contact of the gauze pad with the gums and alveolar socket after intraoral surgery is performed. Such direct contact is fundamental for the uneventful healing process that is highly sought to provide high quality treatment.

Figure 30:
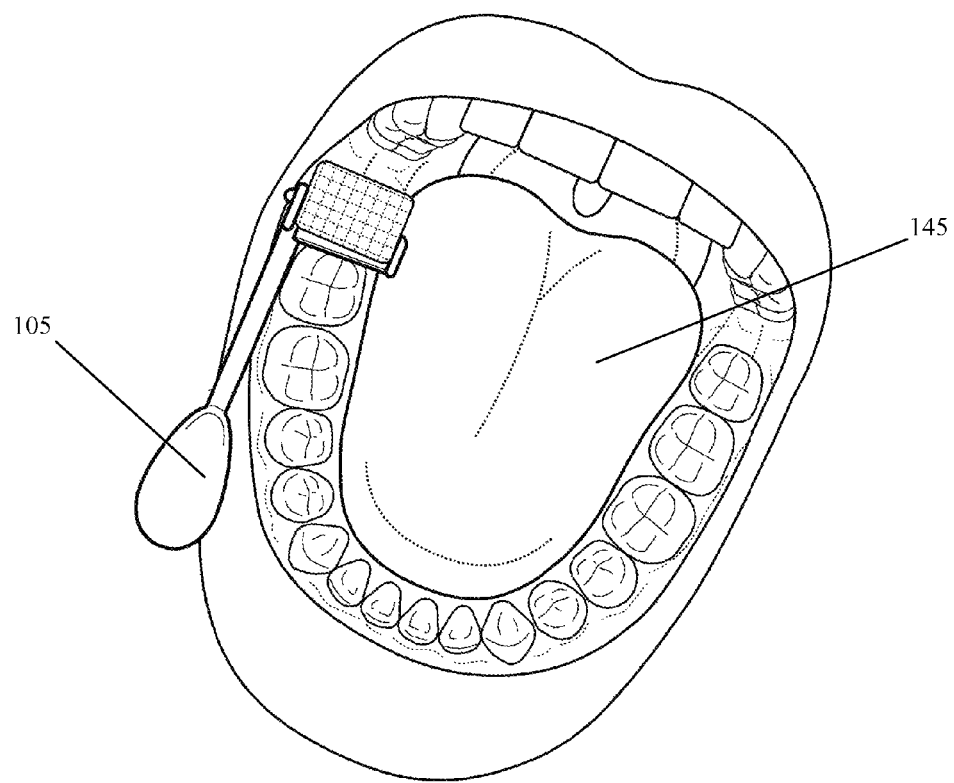
FIG. 30 shows a diagrammatical representation in perspective view of the post-surgical use of the embodiment of the gauze pad holder illustrated in FIG. 21 in a socket of a molar tooth site.
Figure 31:
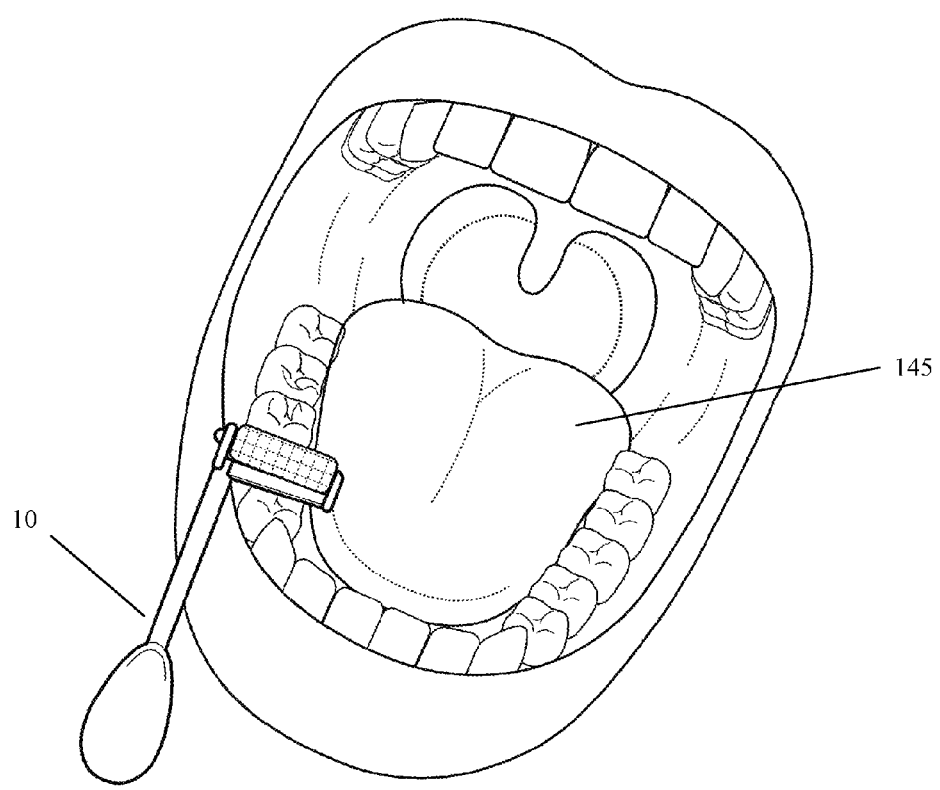
FIG. 31 shows a diagrammatical representation in perspective view of the post-surgical use of the embodiment of the gauze pad holder illustrated in FIG. 3 in a socket of a premolar tooth site.
Figure 32:
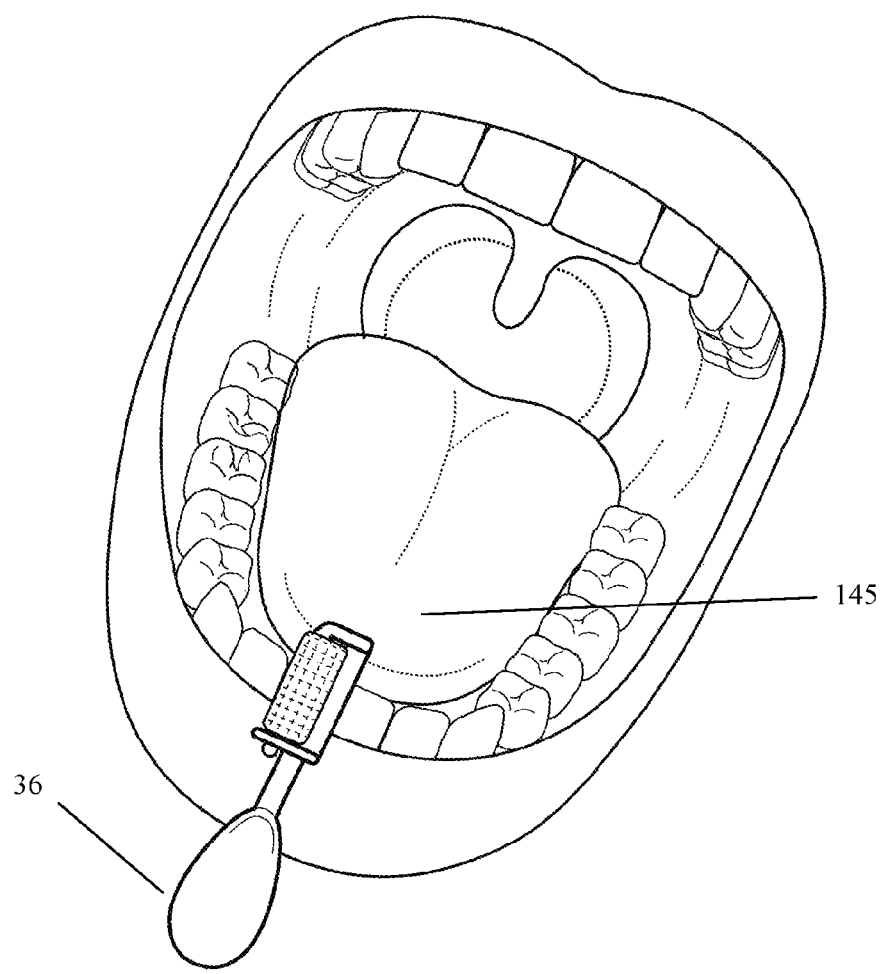
FIG. 32 shows a diagrammatical representation in perspective view of the post-surgical use of the embodiment of the gauze pad holder illustrated in FIG. 9, used on a socket after the surgical procedure on the anterior tooth site.

FIGS. 30, 31 and 32 illustrate the placing of the holder and gauze pad herein disclosed in the patient's mouth 145. FIG. 30 illustrates, as an example, the embodiment 105 on a socket after an extraction or surgical procedure has been done in a molar tooth site. Embodiments 10, 27 and 130 may also be used in a socket of a molar tooth site as illustrated in FIG. 30 using embodiment 105. Similarly, FIG. 31 shows the use of embodiment types 10, 27, 100 and 125 on a socket after a surgical procedure or extraction has been performed in a premolar tooth site, using embodiment 10 as the exemplary embodiment. Alternatively, as illustrated in FIG. 32 using embodiment 36 as example in the illustration, embodiments 36, 52, 60 or 85 are preferably used on a socked after the surgical procedure on the anterior teeth site.

Figure 33:
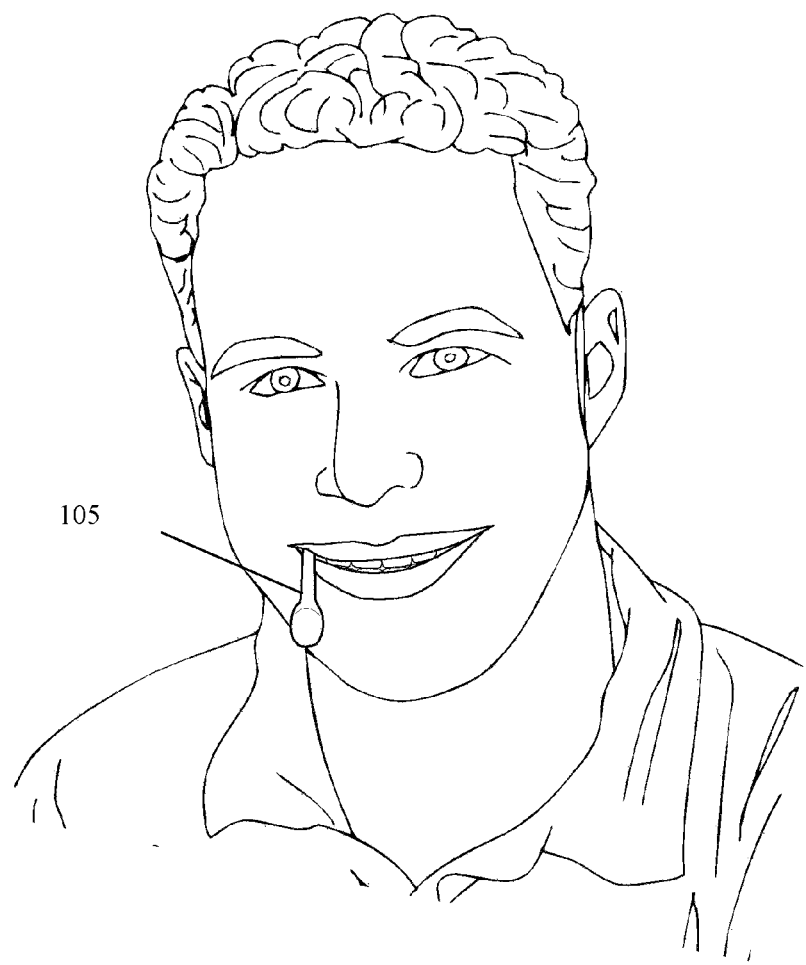
FIG. 33 shows a diagrammatical representation of a patient with closed mouth and using any of the gauze pad holder embodiments herein disclosed on the post-surgical use on a molar or premolar tooth site.
Figure 34:
FIG. 34 shows a diagrammatical representation of a patient with closed mouth and using any of the gauze pad holder embodiments herein disclosed on the post-surgical use on an anterior tooth site.

After the pad already assembled in the particular holder is placed on the pertinent surgical area, the patient presses the gauze pad by closing the jaws as illustrated in FIGS. 33 and 34, said gauze pad should be maintained in the surgical area for about 30 minutes to maintain a dry field and allow the blood clot to form. As indicated previously, each type of embodiment is ergonomically designed according to the anatomy of the oral cavity and the surroundings of the given surgical site.

While the patient is using the herein described holder, the patient may secure said holder at any given time if necessary by holding the handle section, thus the patient may even talk carefully without the gauze pad being displaced from its holder. If necessary, the gauze pad holder and its gauze may be substituted by a new one by just repeating the described process.

Figure 35:
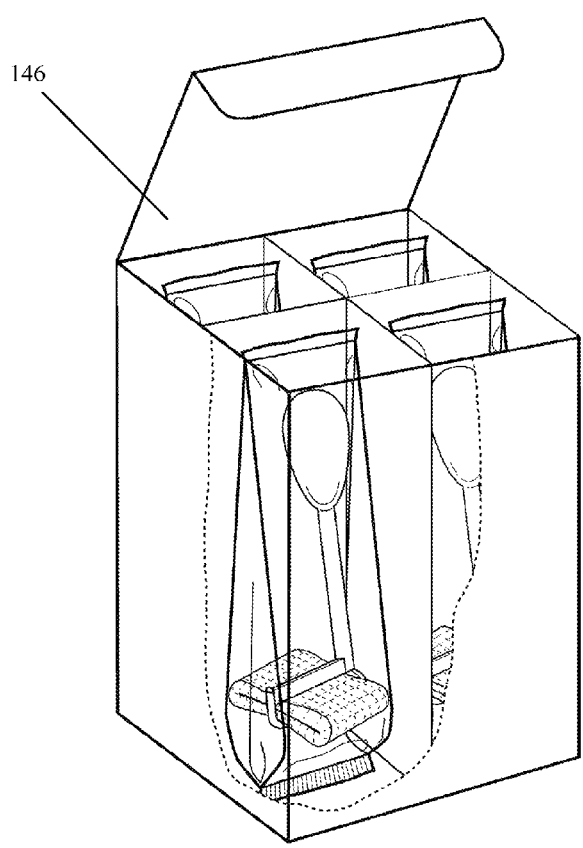
FIG. 35 illustrates a diagrammatical representation of sanitary and disposable kit having a predetermined amount of units comprising a holder illustrated in FIG. 3, wherein the enclosure of said kit has been cut off in order to shows its details.
Figures 37, 38:
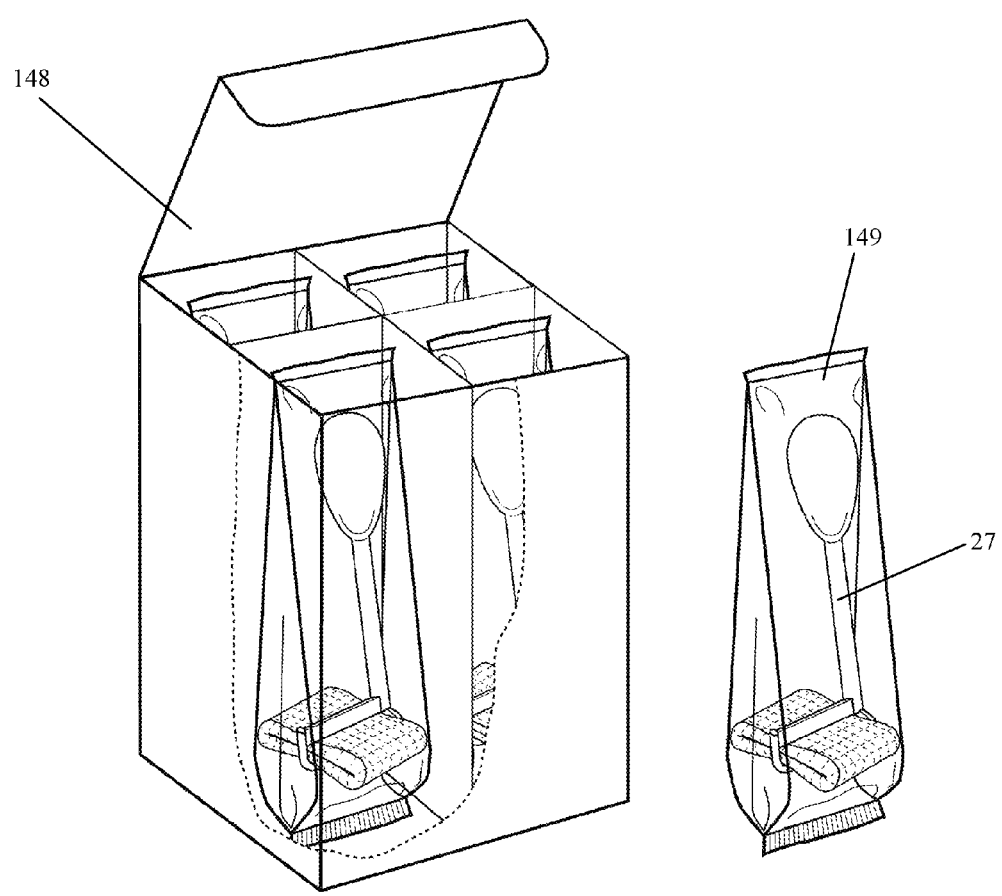
FIG. 37 illustrates a diagrammatical representation of sanitary and disposable kit having a predetermined amount of units comprising a holder illustrated in FIG. 6, wherein the enclosure of said kit has been cut off in order to shows its details.
FIG. 38 shows a diagrammatical representation of individually wrapped embodiment of the pad holder illustrated in FIG. 6 and enclosed in the sanitary and disposable kit illustrated in FIG. 37.
Figure 39:
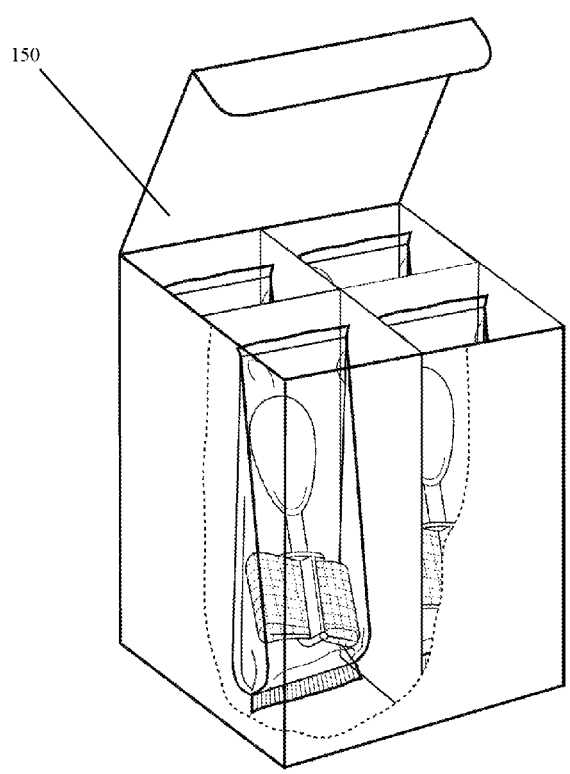
FIG. 39 illustrates a diagrammatical representation of sanitary and disposable kit having a predetermined amount of units comprising a holder illustrated in FIG. 9, wherein the enclosure of said kit has been cut off in order to shows its details.
Figure 41:
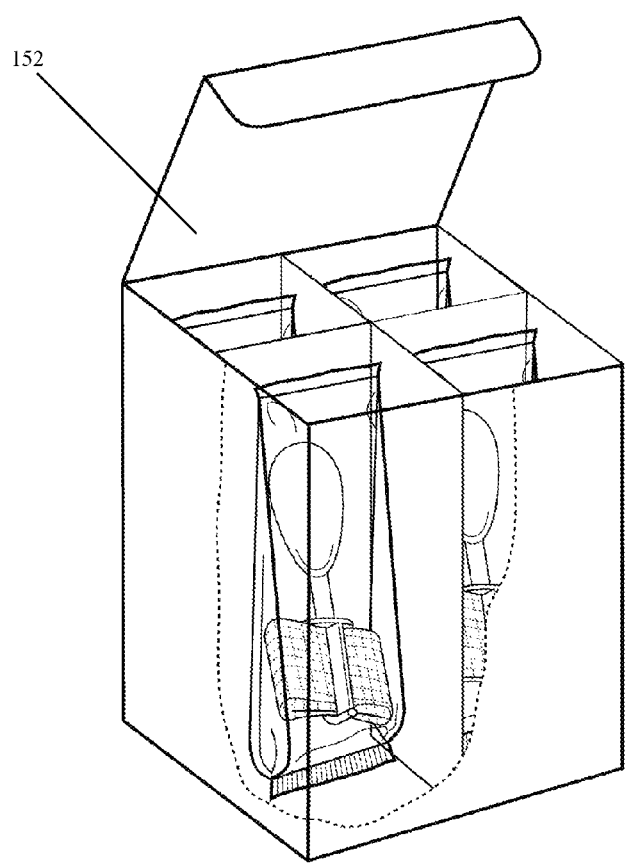
FIG. 41 illustrates a diagrammatical representation of sanitary and disposable kit having a predetermined amount of units comprising a holder illustrated in FIG. 12, wherein the enclosure of said kit has been cut off in order to shows its details.
Figure 45:
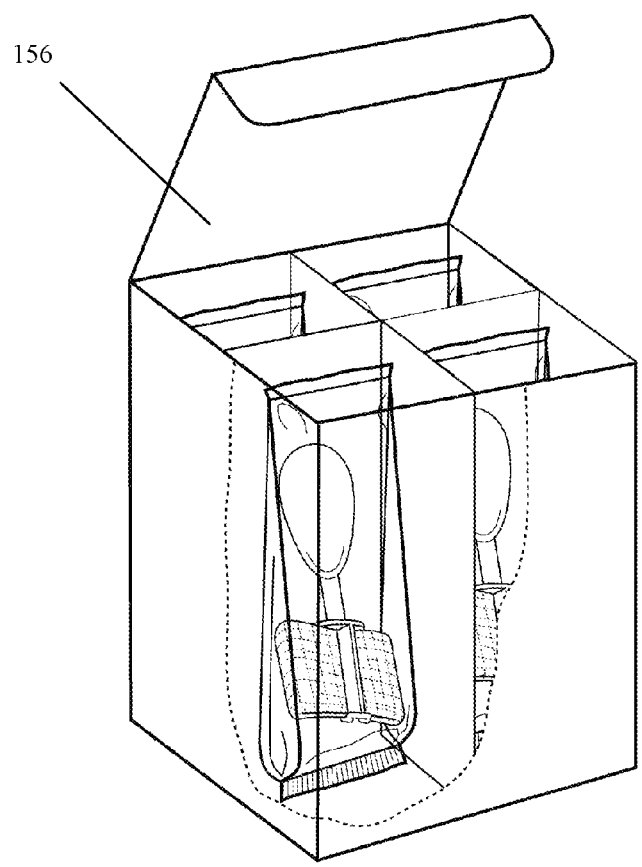
FIG. 45 illustrates a diagrammatical representation of sanitary and disposable kit having a predetermined amount of units comprising a holder illustrated in FIG. 18, wherein the enclosure of said kit has been cut off in order to shows its details.
Figure 46:
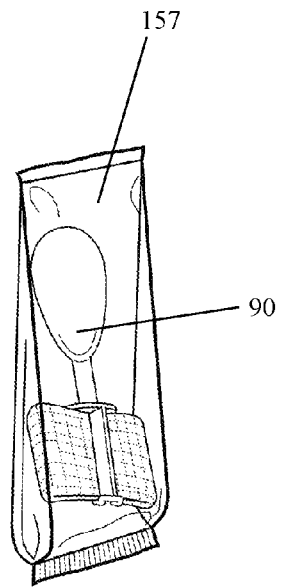
FIG. 46 shows a diagrammatical representation of individually wrapped embodiment of the pad holder illustrated in FIG. 18 and enclosed in the sanitary and disposable kit illustrated in FIG. 45.
Figure 47:
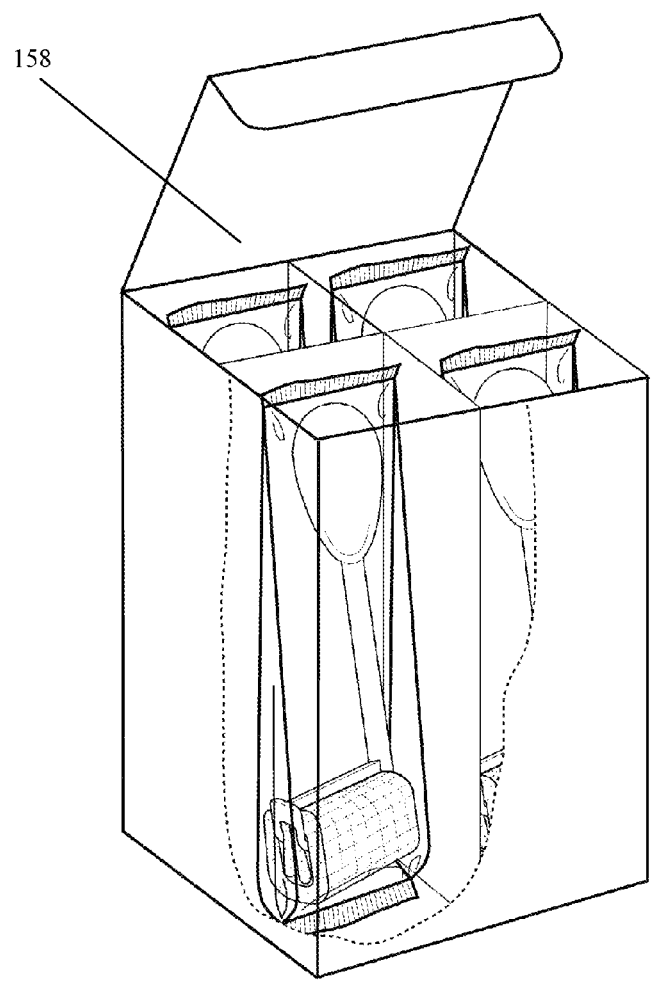
FIG. 47 illustrates a diagrammatical representation of sanitary and disposable kit having a predetermined amount of units comprising a holder illustrated in FIG. 21, wherein the enclosure of said kit has been cut off in order to shows its details.
Figure 49:
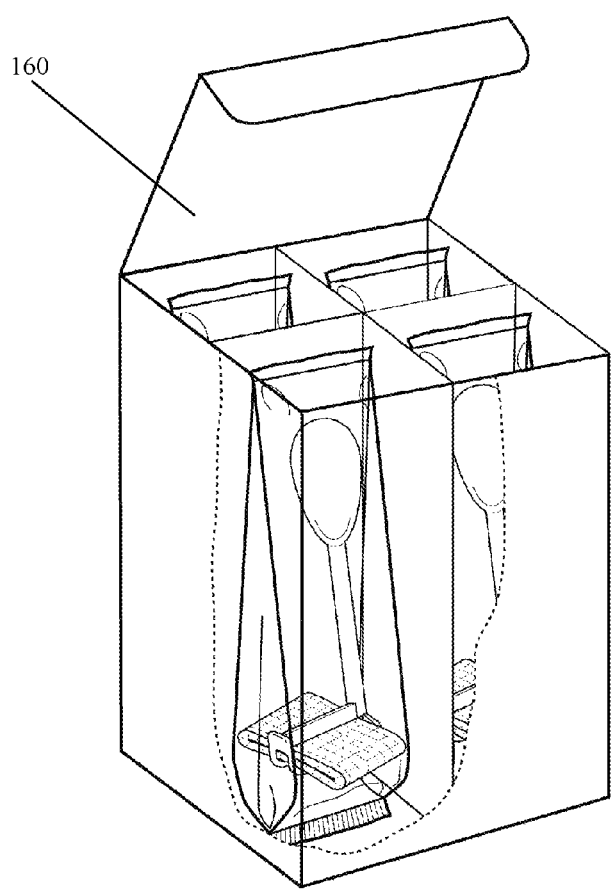
FIG. 49 illustrates a diagrammatical representation of sanitary and disposable kit having a predetermined amount of units comprising a holder illustrated in FIG. 22, wherein the enclosure of said kit has been cut off in order to shows its details.
Figures 51, 52:
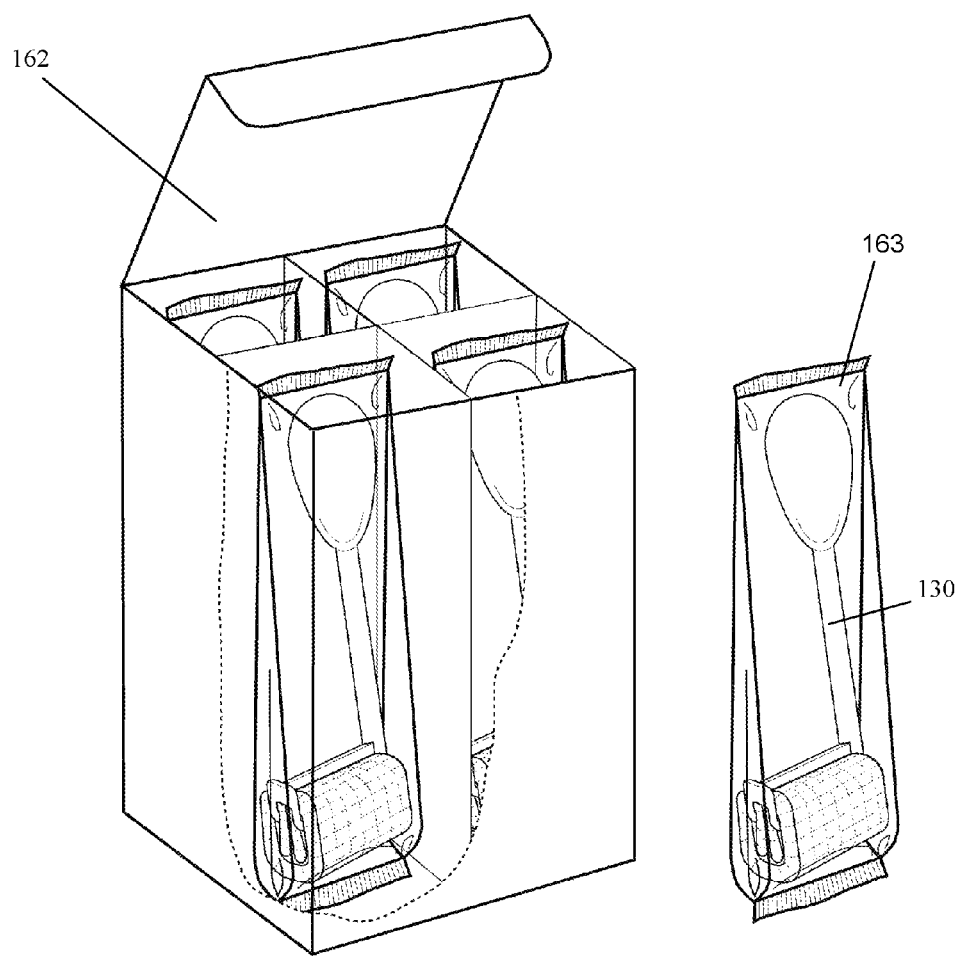
FIG. 51 illustrates a diagrammatical representation of sanitary and disposable kit having a predetermined amount of units comprising a holder illustrated in FIG. 25, wherein the enclosure of said kit has been cut off in order to shows its details.
FIG. 52 shows a diagrammatical representation of individually wrapped embodiment of the pad holder illustrated in FIG. 25 and enclosed in the sanitary and disposable kit illustrated in FIG. 51.

It is also contemplated that the embodiments 10, 27, 36, 54, 65, 90, 105 and 130 or any other embodiments within the scope of the instant invention may be sold in enclosed, sanitary and hygienic kits or packages as illustrated in FIG. 35 for embodiment 10; FIG. 37 for embodiment 27, FIG. 39 for embodiment 36, FIG. 41 for embodiment 54, FIG. 43 for embodiment 65; FIG. 45 for embodiment 90, FIGS. 47 and 49 for embodiment 105 and FIGS. 51 and 53 for embodiment 130.

Figure 36:
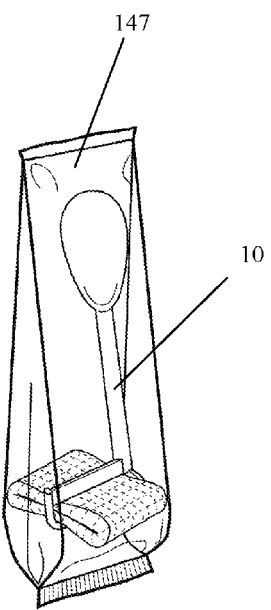
FIG. 36 shows a diagrammatical representation of individually wrapped embodiment of the pad holder illustrated in FIG. 3 and enclosed in the sanitary and disposable kit illustrated in FIG. 35.
Figure 40:
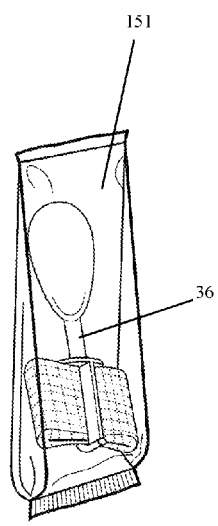
FIG. 40 shows a diagrammatical representation of individually wrapped embodiment of the pad holder illustrated in FIG. 9 and enclosed in the sanitary and disposable kit illustrated in FIG. 39.
Figure 42:
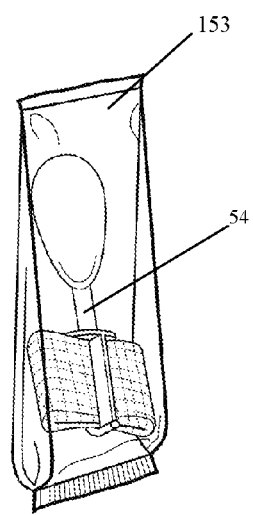
FIG. 42 shows a diagrammatical representation of individually wrapped embodiment of the pad holder illustrated in FIG. 12 and enclosed in the sanitary and disposable kit illustrated in FIG. 41.
Figures 43, 44:
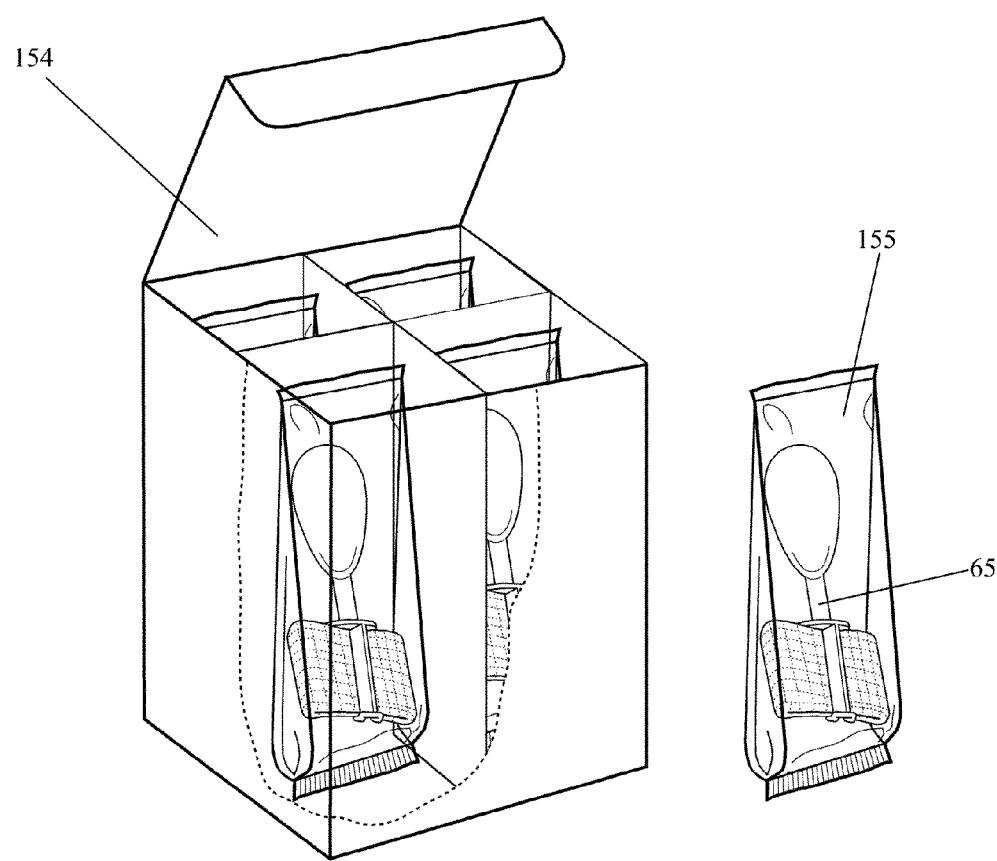
FIG. 43 illustrates a diagrammatical representation of sanitary and disposable kit having a predetermined amount of units comprising a holder illustrated in FIG. 15, wherein the enclosure of said kit has been cut off in order to shows its details.
FIG. 44 shows a diagrammatical representation of individually wrapped embodiment of the pad holder illustrated in FIG. 15 and enclosed in the sanitary and disposable kit illustrated in FIG. 43.
Figure 48:
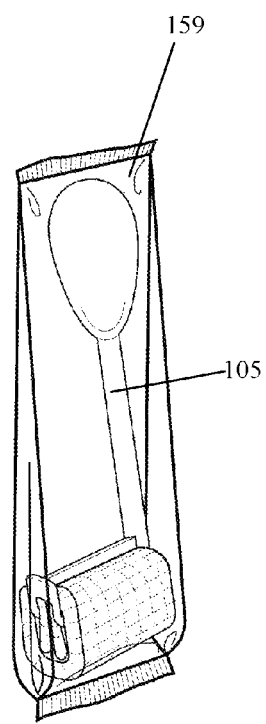
FIG. 48 shows a diagrammatical representation of individually wrapped embodiment of the pad holder illustrated in FIG. 21 and enclosed in the sanitary and disposable kit illustrated in FIG. 47.
Figure 50:
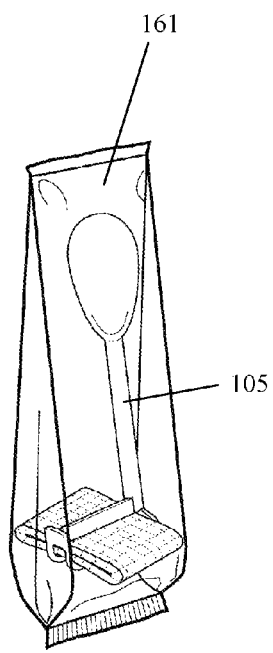
FIG. 50 shows a diagrammatical representation of individually wrapped embodiment of the pad holder illustrated in FIG. 22 and enclosed in the sanitary and disposable kit illustrated in FIG. 49.

Each of said kits comprise multiple individually wrapped gauze pads that have been already and properly disinfected and sanitized by known methods in the art and each pad being already assembled to the disclosed holder as illustrated in FIG. 36 for embodiment 10, FIG. 38 for embodiment 27, FIG. 40 for embodiment 36, FIG. 42 for embodiment 54; FIG. 44 for embodiment 65, FIG. 45 for embodiment 90, FIGS. 48 and 50 for embodiment 105 and FIGS. 52 and 54 for embodiment 130 in order to avoid potential health risks caused by microorganism such as germs and/or bacteria.

Although the invention has been described and illustrated in detail, it is to be clearly understood that such description is for purposes of illustration and example and it is not intended to be taken by way of limitation. For instance, some sections of the gauze holder such as the elongated body, the handle and the holding unit may have alternatives shapes and/or configurations and still be within the spirit of the invention. Therefore, it is recognized that multiple variations exist, including both narrowing and broadening variations of the appended claims.

What is claimed is:

1. A holder, useful in holding a gauze pad in site after an intraoral surgical procedure, said holder comprising:
   (a) a handle section comprising an oval-shaped body, said oval-shaped body comprising:
      (1) a concave center;
      (2) round edges surrounding said concave center; and
   (b) a connecting section comprising an elongated body, said elongated body comprising:
      (1) a first end;
      (2) a second end; and
   (c) a first holding section comprising a flat main body; said flat main body comprising:
      (1) a center;
      (2) a flat front surface;
      (3) a flat back surface located in opposite position to said flat front surface;
      (4) a round aperture at the center of said main flat body; said round aperture passing through the flat front surface to the flat back surface of said main flat body; and
   (d) a supporting section comprising of an elongated body, said elongated body comprising:
      (1) a first end;
      (2) a second end; and
   (e) a second holding section comprising a cylindrical elongated flexible body, said cylindrical elongated flexible body comprising:
      (1) a first end;
      (2) a second end; and
   (f) a sphere-shaped section; and
wherein:
   (1) the first end of the elongated body of the connecting section is connected to said handle section;
   (2) the second end of the elongated body of the connecting section is connected to said flat main body of the first holding section in an aligned position with reference to said handle section;
   (3) the first end of the elongated body of said supporting section is perpendicularly connected to the second end of the elongated body of the connecting section;
   (4) the second end of the elongated body of said supporting section is connected perpendicularly to the first end of the cylindrical elongated flexible body of the second holding section;
   (5) the second end of the cylindrical elongated flexible body of the second holding section is connected to the sphere shaped section; and
wherein:
   the described connections between: the handle section (a), the connecting section (b), the first holding section (c), the supporting section (d); the second holding section (e) and the sphere-shaped section (f) constitute and provide a single integral structure; and
wherein:
   an internal cavity, capable of holding a gauze pad and located in a perpendicular position to the handle section, the connecting section and the first holding section is created by inserting the sphere-shaped section into the round aperture on the first holding section, thus allowing the sphere-shaped section to pass throughout the flat front surface to the flat back surface of the flat main body of the first holding section.

2. The holder as recited in claim 1, further comprising a wedge-shaped groove in open and direct communication with the round aperture on the flat main body of the first holding section.

3. The holder as recited in claim 1, wherein the handle section has a flat surface.

4. The holder of claim 1, wherein the elongated body of said connecting section is cylindrical.

5. The holder as recited in claim 1, wherein said holder is made of plastic.

6. The holder as recited in claim 2, wherein the handle section has a flat surface.

7. The holder of claim 2, wherein the elongated body of said connecting section is cylindrical.

8. The holder as recited in claim 2, wherein said holder is made of plastic.

9. A holder, useful in holding a gauze pad in site after an intraoral surgical procedure, said holder comprising:
(a) a handle section comprising an oval-shaped body, said oval-shaped body comprising:
 (1) a concave center;
 (2) round edges surrounding said concave center; and
(b) a connecting section having an elongated body, said connecting section comprising:
 (1) a first end;
 (2) a second end; and
(c) a first holding section comprising a flat main body; said flat main body comprising:
 (1) a center;
 (2) a flat front surface;
 (3) a flat back surface located in opposite position to said flat front surface;
 (4) a round aperture at the center of said main flat body; said round aperture passing through the flat front surface to the flat back surface of said main flat body; and
(d) a supporting section comprising of an elongated body, said elongated body comprising:
 (1) a first end;
 (2) a second end; and
(e) a second holding section comprising a cylindrical elongated flexible body, said cylindrical elongated flexible body comprising:
 (1) a first end;
 (2) a second end; and
(f) a sphere-shaped section; and
wherein:
 (1) the first end of the elongated body of the connecting section is connected to said handle section;
 (2) the second end of the elongated body of the connecting section is connected to the flat front surface of said flat main body of the first holding section in an aligned position with reference to said handle section;
 (3) the first end of the elongated body of said supporting section is connected to the flat back surface of said main flat body of the first holding section in an aligned position to the handle section and the connecting section;
 (4) the second end of the elongated body of said supporting section is connected perpendicularly to the first end of the cylindrical elongated flexible body of the second holding section;
 (5) the second end of the cylindrical elongated flexible body of the second holding section is connected to the sphere-shaped section; and
wherein:
 the described connections between: the handle section (a), the connecting section (b), the first holding section (c), the supporting section (d); the second holding section (e) and the sphere-shaped section (f) constitute and provide a single integral structure; and
wherein:
 an internal cavity, capable of holding a gauze pad and located in a aligned position to the handle section, the connecting section and the first holding section is created by inserting the sphere-shaped section into the round aperture located on the first holding section, thus allowing the sphere-shaped section to pass throughout the flat back surface to the flat front surface of the main flat body of the first holding section.

10. The holder as recited in claim 9, further comprising a wedge-shaped groove in open and direct communication with the round aperture on the flat main body of the first holding section.

11. The holder as recited in claim 9, wherein the handle section has a flat surface.

12. The holder of claim 9, wherein the elongated body of said connecting section is cylindrical.

13. The holder as recited in claim 9, wherein said holder is made of plastic.

14. The holder as recited in claim 10, wherein the handle section has a flat surface.

15. The holder of claim 10, wherein the elongated body of said connecting section is cylindrical.

16. The holder as recited in claim 10, wherein said holder is made of plastic.

17. A holder, useful in holding a gauze pad in site after an intraoral surgical procedure, said holder comprising:
(a) a handle section comprising an oval-shaped body, said oval-shaped body comprising:
 (1) a concave center;
 (2) round edges surrounding said concave center; and
(b) a connecting section having an elongated body, said elongated body comprising:
 (1) a first end;
 (2) a second end; and
(c) a first holding section comprising a flat main body; said flat main body comprising:
 (1) a center;
 (2) a flat front surface;
 (3) a flat back surface, located in opposite position to said flat front surface,
 (4) a first round aperture near the center of said main flat body, said first round aperture passing through the flat front surface to the flat back surface of said main flat body;
 (4) a second round aperture near the center of said main flat body, said second round aperture passing through the flat front surface to the flat back surface of said main flat body; and
(d) a supporting section comprising of an elongated body, said elongated body comprising:
 (1) a first end;
 (2) a second end; and
(e) a second holding section, said second holding section comprising a:
 (1) a base section;
 (2) a first cylindrical elongated flexible body, said first cylindrical elongated flexible body comprising:
  (a) a first end;
  (b) a second end; and
 (3) a second cylindrical elongated flexible body, said second cylindrical elongated flexible body comprising:
  (a) a first end;
  (b) a second end; and
(f) a first spherical section; and
(g) a second spherical section; and
wherein:
 (1) the first end of the elongated body of the connecting section is connected to said handle section;
 (2) the second end of the elongated body of the connecting section is connected to the flat front surface of said flat main body of the first holding section in an aligned position to said handle section;

(3) the first end of the elongated body of said supporting section is connected in a parallel position to the flat back flat surface of said flat main body of the first holding section;

(4) the second end of the elongated body of said supporting section is connected perpendicularly to the base section of the second holding section; and (5) the first end of the first cylindrical elongated flexible body of the second holding section is connected perpendicularly to the base section;

(6) the first end of the second cylindrical elongated flexible body of the second holding section is connected perpendicularly to the base section and in a parallel position with reference to the first cylindrical elongated body of said second holding section;

(7) the second end of the first cylindrical elongated flexible body of the second holding section is connected to the first spherical section;

(8) the second end of the second cylindrical elongated flexible body of the second holding section is connected to the second sphere-shaped section; and wherein:

the described connections between: the handle section (a), the connecting section (b), the first holding section (c), the supporting section (d); the second holding section (e) and the sphere-shaped sections (f) and (g) constitute and provide a single integral structure; and wherein:

an internal cavity, capable of holding a gauze pad and located in an aligned position to the handle section, the connecting section and the first holding section is created by inserting the first sphere-shaped section into the first round aperture located on the first holding section and inserting the second sphere-shaped section into the second round aperture located on the first holding section, thus allowing the first sphere-shaped section and the second sphere shaped section to pass throughout the flat back surface to the flat front surface of the main flat body of the first holding section.

18. The holder as recited in claim 17, wherein the handle section has a flat surface.

19. The holder of claim 17, wherein the elongated body of said connecting section is cylindrical.

20. The holder as recited in claim 17, wherein said holder is made of plastic.

21. A holder, useful in holding a gauze pad in site after an intraoral surgical procedure, said holder comprising:

(a) a handle section comprising an oval-shaped body, said oval-shaped body comprising:
  (1) a concave center;
  (2) round edges surrounding said concave center; and
(b) a connecting section having an elongated body, said elongated body comprising:
  (1) a first end;
  (2) a second end; and
(c) a first holding section comprising flat main body; said flat main body comprising:
  (1) a center;
  (2) a flat front surface;
  (3) a flat back surface, located in opposite position to said flat front surface,
  (4) a first round aperture near the center of said main flat body, said first round aperture passing through the flat front surface to the flat back surface of said main flat body;
  (4) a second round aperture near the center of said main flat body, said second round aperture passing through the flat front surface to the flat back surface of said main flat body;
  (5) a first wedge-shaped groove in open and direct communication with said first round aperture;
  (6) a second wedge shaped groove in open and direct communication with said second aperture; and
(d) a supporting section comprising of an elongated body, said elongated body comprising:
  (1) a first end;
  (2) a second end; and
(e) a second holding section, said second holding section comprising a:
  (1) a base section;
  (2) a first cylindrical elongated flexible body, said first cylindrical elongated flexible body comprising:
    (a) a first end;
    (b) a second end; and
  (3) a second cylindrical elongated flexible body, said second cylindrical elongated flexible body comprising:
    (a) a first end;
    (b) a second end; and
(f) a first spherical section; and
(g) a second spherical section; and wherein:

(1) the first end of the elongated body of the connecting section is connected to said handle section;

(2) the second end of the elongated body of the connecting section is connected to the flat front surface of said flat main body of the first holding section in an aligned position to said handle section;

(3) the first end of the elongated body of said supporting section is connected in a parallel position to the flat back surface of said flat main body of the first holding section;

(4) the second end of the elongated body of said supporting section is connected perpendicularly to the base section of the second holding section; and (5) the first end of the first cylindrical elongated flexible body of the second holding section is connected perpendicularly to the base section;

(6) the first end of the second cylindrical elongated flexible body of the second holding section is connected perpendicularly to the base section and in a parallel position with reference to the first cylindrical elongated body of said second holding section;

(7) the second end of the first cylindrical elongated flexible body of the second holding section is connected to the first spherical section;

(8) the second end of the second cylindrical elongated flexible body of the second holding section is connected to the second spherical section; and wherein:

the described connections between: the handle section (a), the connecting section (b), the first holding section (c), the supporting section (d); the second holding section (e) and the spherical sections (f) and (g) constitute and provide a single integral structure; and wherein:

an internal cavity, capable of holding a gauze pad and located in a aligned position to the handle section, the connecting section and the first holding section is created by inserting the first spherical section into the first round aperture via the first wedge-shaped groove located on the first holding section and inserting the second spherical section into the second round aperture via the second wedge-shaped groove located on the first holding section, thus allowing the first spherical section and the second spherical section to pass throughout the flat back surface to the flat first surface of the main flat body of the first holding section.

22. The holder as recited in claim 21, wherein the handle section has a flat surface.

23. The holder of claim 21, wherein the elongated body of said connecting section is cylindrical.

24. The holder as recited in claim 21, wherein said holder is made of plastic.

25. A holder, useful in holding a gauze pad in site after an intraoral surgical procedure, said holder comprising:
   (a) a handle section comprising an oval-shaped body, said oval-shaped body comprising:
      (1) a concave center;
      (2) round edges surrounding said concave center; and
   (b) a connecting section comprising an elongated body, said elongated body comprising:
      (1) a first end;
      (2) a second end; and
   (c) a first holding section comprising a flat main body; said flat main body comprising:
      (1) a center;
      (2) a flat front surface;
      (3) a flat back surface located in opposite position to said flat front surface;
      (4) a first round aperture near the center of said main flat body; said first round aperture passing through the flat front surface to the flat back surface of said main flat body;
      (4) a second round aperture near the center of said main flat body; said second round aperture passing through the flat front surface to the flat back surface of said main flat body;
   (d) a supporting section comprising of an elongated body, said elongated body comprising:
      (1) a first end;
      (2) a second end; and
   (e) a second holding section, said second holding section comprising a:
      (1) a base section;
      (2) a first cylindrical elongated flexible body, said first cylindrical elongated flexible body comprising:
         (a) a first end;
         (b) a second end;
      (3) a second cylindrical elongated flexible body, said second cylindrical elongated flexible body comprising:
         (a) a first end;
         (b) a second end;
   (f) a first sphere-shaped section;
   (g) a second sphere-shaped section; and
wherein:
   (1) the first end of the elongated body of the connecting section is connected to said handle section;
   (2) the second end of the elongated body of the connecting section is connected to said flat main body of the first holding section in an aligned position with reference to said handle section;
   (3) the first end of the elongated body of said supporting section is perpendicularly connected to the second end of the elongated body of the connecting section;
   (4) the second end of the elongated body of said supporting section is connected perpendicularly to the base section of the second holding section;
   (5) the first end of the first cylindrical elongated flexible body of the second holding section is connected perpendicularly to the base section;
   (6) the first end of the second cylindrical elongated flexible body of the second holding section is connected perpendicularly to the base section and in a parallel position with reference to the first cylindrical elongated body of said second holding section;
   (7) the second end of the first cylindrical elongated flexible body of the second holding section is connected to the first sphere-shaped section;
   (8) the second end of the second cylindrical elongated flexible body of the second holding section is connected to the second sphere-shaped section; and
wherein:
   the described connections between: the handle section (a), the connecting section (b), the first holding section (c), the supporting section (d); second holding section (e) and the sphere-shaped section (f) constitute and provide a holder having single integral structure; and
wherein:
   an internal cavity, capable of holding a gauze pad and located in a perpendicular position to the handle section, the connecting section and the first holding section is created by inserting the first sphere-shaped section into the first round aperture located on the first holding section and inserting the second sphere-shaped section into the second round aperture located on the first holding section, thus allowing the first sphere-shaped section and the second sphere-shaped section to pass throughout the flat front surface to the flat back surface of the main flat body of the first holding section.

26. The holder as recited in claim 25, wherein the handle section has a flat surface.

27. The holder of claim 25, wherein the elongated body of said connecting section is cylindrical.

28. The holder as recited in claim 25, wherein said holder is made of plastic.

29. A holder, useful in holding a gauze pad in site after an intraoral surgical procedure, said holder comprising:
   (a) a handle section comprising an oval-shaped body, said oval-shaped body comprising:
      (1) a concave center;
      (2) round edges surrounding said concave center; and
   (b) a connecting section comprising an elongated body, said elongated body comprising:
      (1) a first end;
      (2) a second end; and
   (c) a first holding section comprising a flat main body; said flat main body comprising:
      (1) a center;
      (2) a flat front surface;
      (3) a flat back surface located in opposite position to said flat front surface;
      (4) a first round aperture near the center of said main flat body; said first round aperture passing through the flat front surface to the flat back surface of said main flat body;
      (4) a second round aperture near the center of said main flat body; said second round aperture passing through the flat front surface to the flat back surface of said main flat body;
      (5) a first wedge-shaped groove in open and direct communication with said first round aperture;

(6) a second wedge shaped groove in open and direct communication with said second aperture; and
(d) a supporting section comprising of an elongated body, said elongated body comprising:
(1) a first end;
(2) a second end; and
(e) a second holding section, said second holding section comprising a:
(1) a base section;
(2) a first cylindrical elongated flexible body, said first cylindrical elongated flexible body comprising:
(a) a first end;
(b) a second end;
(3) a second cylindrical elongated flexible body, said second cylindrical elongated flexible body comprising:
(a) a first end;
(b) a second end;
(f) a first sphere-shaped section;
(g) a second sphere-shaped section; and
wherein:
(1) the first end of the elongated body of the connecting section is connected to said handle section;
(2) the second end of the elongated body of the connecting section is connected to said flat main body of the first holding section in an aligned position with reference to said handle section;
(3) the first end of the elongated body of said supporting section is perpendicularly connected to the second end of the elongated body of the connecting section;
(4) the second end of the elongated body of said supporting section is connected perpendicularly to the base section of the second holding section;
(5) the first end of the first cylindrical elongated flexible body of the second holding section is connected perpendicularly to the base section;
(6) the first end of the second cylindrical elongated flexible body of the second holding section is connected perpendicularly to the base section and in a parallel position with reference to the first cylindrical elongated body of said second holding section;
(7) the second end of the first cylindrical elongated flexible body of the second holding section is connected to the first sphere-shaped section;
(8) the second end of the second cylindrical elongated flexible body of the second holding section is connected to the second sphere-shaped section; and
wherein:
the described connections between: the handle section (a), the connecting section (b), the first holding section (c), the supporting section (d); second holding section (e) and the sphere-shaped sections (f) and (g) constitute and provide a holder having single integral structure; and
wherein:
an internal cavity, capable of holding a gauze pad and located in a perpendicular position to the handle section, the connecting section and the first holding section is created by inserting the first sphere-shaped section into the first round aperture via the first wedge-shaped groove located on the first holding section and inserting the second sphere-shaped section into the second round aperture via the second wedge-shaped groove located on the first holding section, thus allowing the first sphere-shaped section and the second sphere-shaped section to pass throughout the flat front surface to the flat back surface of the main flat body of the first holding section.

30. The holder as recited in claim 29, wherein the handle section has a flat surface.

31. The holder of claim 29, wherein the elongated body of said connecting section is cylindrical.

32. The holder as recited in claim 29, wherein said holder is made of plastic.

33. A sanitary and disposable kit comprising:
a predetermined amount of individually wrapped units, each comprising:
a holder as recited in claim 1;
a gauze pad already assembled and properly assembled and secured on the internal cavity of said holder; and
an enclosure containing said predetermined amount of individually wrapped units.

34. A sanitary and disposable kit comprising:
a predetermined amount of individually wrapped units, each comprising:
a holder as recited in claim 2;
a gauze pad already assembled and properly assembled and secured on the internal cavity of said holder; and
an enclosure containing said predetermined amount of individually wrapped units.

35. A sanitary and disposable kit comprising:
a predetermined amount of individually wrapped units, each comprising:
a holder as recited in claim 9;
a gauze pad already assembled and properly assembled and secured on the internal cavity of said holder; and
an enclosure containing said predetermined amount of individually wrapped units.

36. A sanitary and disposable kit comprising:
a predetermined amount of individually wrapped units, each comprising:
a holder as recited in claim 10;
a gauze pad already assembled and properly assembled and secured on the internal cavity of said holder; and
an enclosure containing said predetermined amount of individually wrapped units.

37. A sanitary and disposable kit comprising:
a predetermined amount of individually wrapped units, each comprising:
a holder as recited in claim 17;
a gauze pad already assembled and properly assembled and secured on the internal cavity of said holder; and
an enclosure containing said predetermined amount of individually wrapped units.

38. A sanitary and disposable kit comprising:
a predetermined amount of individually wrapped units, each comprising:
a holder as recited in claim 21;
a gauze pad already assembled and properly assembled and secured on the internal cavity of said holder; and
an enclosure containing said predetermined amount of individually wrapped units.

39. A sanitary and disposable kit comprising:
a predetermined amount of individually wrapped units, said units comprising:
a holder as recited in claim 25;
a gauze pad already assembled and properly assembled and secured on the internal cavity of said holder; and
an enclosure containing said predetermined amount of individually wrapped units.

40. A sanitary and disposable kit comprising:
- a predetermined amount of individually wrapped units, each comprising:
  - a holder as recited in claim 29;
  - a gauze pad already assembled and properly assembled and secured on the internal cavity of said holder; and
- an enclosure containing said predetermined amount of individually wrapped units.

\* \* \* \* \*